US011747205B2

(12) United States Patent
Litvinova

(10) Patent No.: US 11,747,205 B2
(45) Date of Patent: Sep. 5, 2023

(54) NONINVASIVE, MULTISPECTRAL-FLUORESCENCE CHARACTERIZATION OF BIOLOGICAL TISSUES WITH MACHINE/DEEP LEARNING

(71) Applicant: Deep Smart Light Limited, Hemel Hempstead (GB)

(72) Inventor: Karina Litvinova, Hemel Hempstead (GB)

(73) Assignee: Deep Smart Light Ltd., Hemel Hempstead (GB)

( * ) Notice: Subject to any disclaimer, the term of this patent is extended or adjusted under 35 U.S.C. 154(b) by 708 days.

(21) Appl. No.: 16/798,001

(22) Filed: Feb. 21, 2020

(65) Prior Publication Data

US 2020/0268252 A1 Aug. 27, 2020

Related U.S. Application Data

(60) Provisional application No. 62/811,122, filed on Feb. 27, 2019.

(51) Int. Cl.
*G01J 3/44* (2006.01)
*A61B 5/00* (2006.01)
(Continued)

(52) U.S. Cl.
CPC ...... *G01J 3/4406* (2013.01); *A61B 1/000096* (2022.02); *A61B 1/043* (2013.01);
(Continued)

(58) Field of Classification Search
CPC ... A61B 5/0071; A61B 1/00009; A61B 1/043; A61B 1/24; A61B 1/2676; A61B 1/307;
(Continued)

(56) References Cited

U.S. PATENT DOCUMENTS 6,135,965 A * 10/2000 Turner ................. A61B 5/0071
600/408
9,795,303 B2 * 10/2017 Panasyuk ............... A61B 5/742
(Continued)

FOREIGN PATENT DOCUMENTS

CN 103209736 B * 3/2018 ............. A61N 5/103
CN 108960093 A * 12/2018
(Continued)

OTHER PUBLICATIONS

Safi et al. 2016 International Journal of Advanced Computer Science and Applications 7 385-395 (Year: 2016).*
(Continued)

*Primary Examiner* — Keith M Raymond
*Assistant Examiner* — Patrick M Mehl
(74) *Attorney, Agent, or Firm* — Pillsbury Winthrop Shaw Pittman LLP

(57) ABSTRACT

Provided is a obtaining an excitation-emission matrix, wherein the excitation-emission matrix is measured with a spectrometer by: illuminating a biological tissue with stimulant light at a first wavelength to cause a first fluorescent emission of light by the biological tissue, measuring a first set of intensities of the first fluorescent emission of light at a plurality of different respective emission wavelengths, illuminating the biological tissue with stimulant light at a second wavelength to cause a second fluorescent emission of light by the biological tissue, and measuring a second set of intensities of the second fluorescent emission of light at a plurality of different respective emission wavelengths; and inferring a classification of the biological tissue or a concentration of a substance in the biological tissue with a multi-layer neural network or other machine learning model.

29 Claims, 10 Drawing Sheets

(51) Int. Cl.

| | |
|---|---|
| *G06N 20/00* | (2019.01) |
| *A61B 1/00* | (2006.01) |
| *A61B 90/00* | (2016.01) |
| *G01J 3/10* | (2006.01) |
| *G01J 3/18* | (2006.01) |
| *G01J 3/02* | (2006.01) |
| *A61B 5/1455* | (2006.01) |
| *A61B 1/04* | (2006.01) |
| *A61B 1/307* | (2006.01) |
| *A61B 1/267* | (2006.01) |
| *A61B 1/24* | (2006.01) |

(52) U.S. Cl.
CPC .............. *A61B 1/24* (2013.01); *A61B 1/2676* (2013.01); *A61B 1/307* (2013.01); *A61B 5/0071* (2013.01); *A61B 5/1455* (2013.01); *A61B 5/444* (2013.01); *A61B 5/7267* (2013.01); *A61B 5/742* (2013.01); *G01J 3/0272* (2013.01); *G01J 3/10* (2013.01); *G01J 3/18* (2013.01); *G06N 20/00* (2019.01); *A61B 5/0075* (2013.01); *A61B 5/4227* (2013.01); *A61B 2090/3614* (2016.02); *A61B 2560/0214* (2013.01); *A61B 2560/0431* (2013.01); *A61B 2560/0475* (2013.01); *A61B 2562/0238* (2013.01)

(58) Field of Classification Search
CPC ..... A61B 5/1455; A61B 5/444; A61B 5/7267; A61B 5/742; A61B 5/0075; A61B 5/4227; A61B 2090/3614; A61B 2560/0214; A61B 2560/0431; A61B 2560/0475; A61B 2562/0238; A61B 5/0064; A61B 2090/365; A61B 2090/371; A61B 2090/372; A61B 2090/373; G01J 3/0272; G01J 3/10; G01J 3/18; G01J 3/4406; G01J 3/0218; G01J 3/0294; G01J 3/14; G01J 3/28; G01J 3/32; G06N 20/00; G06N 3/0454; G06N 3/0472; G06N 3/088; G06N 5/003; G06N 7/005; G06N 20/20; G06N 3/082; G16H 50/20

See application file for complete search history.

(56) References Cited

U.S. PATENT DOCUMENTS

| | | | |
|---|---|---|---|
| 10,522,070 B2 | 12/2019 | Lim et al. | |
| 2002/0016534 A1 | 2/2002 | Trepagnier | |
| 2002/0137993 A1* | 9/2002 | Pickard | A61B 5/0059 600/476 |
| 2004/0010375 A1* | 1/2004 | Schomacker | G01N 21/31 702/19 |
| 2004/0064053 A1* | 4/2004 | Chang | G01N 21/6486 600/478 |
| 2004/0162489 A1 | 8/2004 | Richards-Kortum | |
| 2011/0117025 A1* | 5/2011 | Dacosta | A61B 5/72 435/5 |
| 2012/0130258 A1* | 5/2012 | Taylor | A61B 3/0075 600/476 |
| 2015/0287191 A1 | 10/2015 | Koruga et al. | |
| 2016/0041153 A1 | 2/2016 | Brown et al. | |
| 2017/0109881 A1* | 4/2017 | Avendi | G06T 7/38 |
| 2017/0167980 A1* | 6/2017 | Dimitriadis | A61B 3/14 |
| 2017/0281007 A1 | 10/2017 | Pyun et al. | |
| 2018/0085003 A1* | 3/2018 | Goldring | A61B 5/746 |
| 2018/0098726 A1 | 4/2018 | Pyun et al. | |
| 2018/0206780 A1 | 7/2018 | Pyun et al. | |
| 2019/0015681 A1 | 1/2019 | Pyun et al. | |
| 2019/0246908 A1 | 8/2019 | Pyun et al. | |
| 2019/0246971 A1 | 8/2019 | Pyun et al. | |
| 2019/0375798 A1 | 12/2019 | Glanville | |
| 2020/0372637 A1* | 11/2020 | Ha | G06T 7/11 |
| 2021/0004668 A1* | 1/2021 | Moshovos | G06N 3/0454 |

FOREIGN PATENT DOCUMENTS

| | | | | |
|---|---|---|---|---|
| DE | 102018216392 A1 * | 3/2020 | ........ | G02B 21/0012 |
| WO | WO-2014200928 A1 * | 12/2014 | ........ | G02B 21/0092 |
| WO | WO-2016063063 A1 * | 4/2016 | ........... | A61B 5/0071 |

OTHER PUBLICATIONS

Lucassen et al. 2007 in "Bioengineering of the skin" Chapter 13 p. 177-190 (Year: 2007).*
Wang 2017 Appl. Sci. 7:32-43 12 pages (Year: 2017).*
Karsoliya 2012 International Journal of Engineering Trends and Technology 6 714-717 (Year: 2012).*
International Search Report and Written Opinion in related international application PCT/IB2021/050844 dated Apr. 14, 2021.
Petrou, Ilya, M.D., "Skin cancer imaging device speeds diagnosis," Dermatology Times, Aug. 7, 2019, https://www.dermatologytimes.com/skin-cancer/skin-cancer-imaging-device-speeds-diagnosis (6 pages).
Speclipse website, Feb. 24, 2020, https://www.speclipse.com/ (12 pages).
International Preliminary Report on Patentability in related international application PCT/IB2021/050844 dated Sep. 1, 2022, pp. 1-11.

* cited by examiner

NONINVASIVE, MULTISPECTRAL-FLUORESCENCE CHARACTERIZATION OF BIOLOGICAL TISSUES WITH MACHINE/DEEP LEARNING

CROSS-REFERENCE TO RELATED APPLICATIONS

This patent claims the benefit of U.S. Provisional Patent Application 62/811,122, filed 27 Feb. 2019, titled NONINVASIVE MULTISPECTRAL FLUORESCENCE DIAGNOSTICS WITH DEEP LEARNING NEURAL NETWORK. The entire content of each afore-listed earlier-filed application is hereby incorporated by reference for all purposes.

BACKGROUND

1. Field

The present disclosure relates generally to noninvasive sensing of the chemical constituents of, for example, biological materials and other materials.

2. Description of the Related Art

Fluorescence occurs when materials emit light in response to absorbing electromagnetic radiation. Examples with which the general public has familiarity typically include fluorescent materials that emit visible light upon absorbing ultraviolet light radiation, like from a black light. Often, the fluorescent light includes varying intensities of different wavelengths of light, in a fluorescent spectrum, which corresponds to the perceived color of the fluorescent light. In some cases, such fluorescent spectra are indicative of the material that constitute the illuminated body.

SUMMARY

The following is a non-exhaustive listing of some aspects of the present techniques. These and other aspects are described in the following disclosure.

Some aspects include a method, light-based sensor (e.g., including a fluorescence spectrometer), server, or distributed computing platform with embedded logic in a light-based sensor configured to execute operations including: obtaining an excitation-emission matrix, wherein the excitation-emission matrix is measured with a spectrometer by: illuminating a biological tissue with stimulant light at a first wavelength to cause a first fluorescent emission of light by the biological tissue, measuring a first set of intensities of the first fluorescent emission of light at a plurality of different respective emission wavelengths, illuminating the biological tissue with stimulant light at a second wavelength to cause a second fluorescent emission of light by the biological tissue, and measuring a second set of intensities of the second fluorescent emission of light at a plurality of different respective emission wavelengths; inferring a classification of the biological tissue or a concentration of a substance in the biological tissue with a machine learning model trained on excitation-emission matrices in a labeled training set with supervised learning; and storing the classification of the biological tissue or the concentration of the substance in memory.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
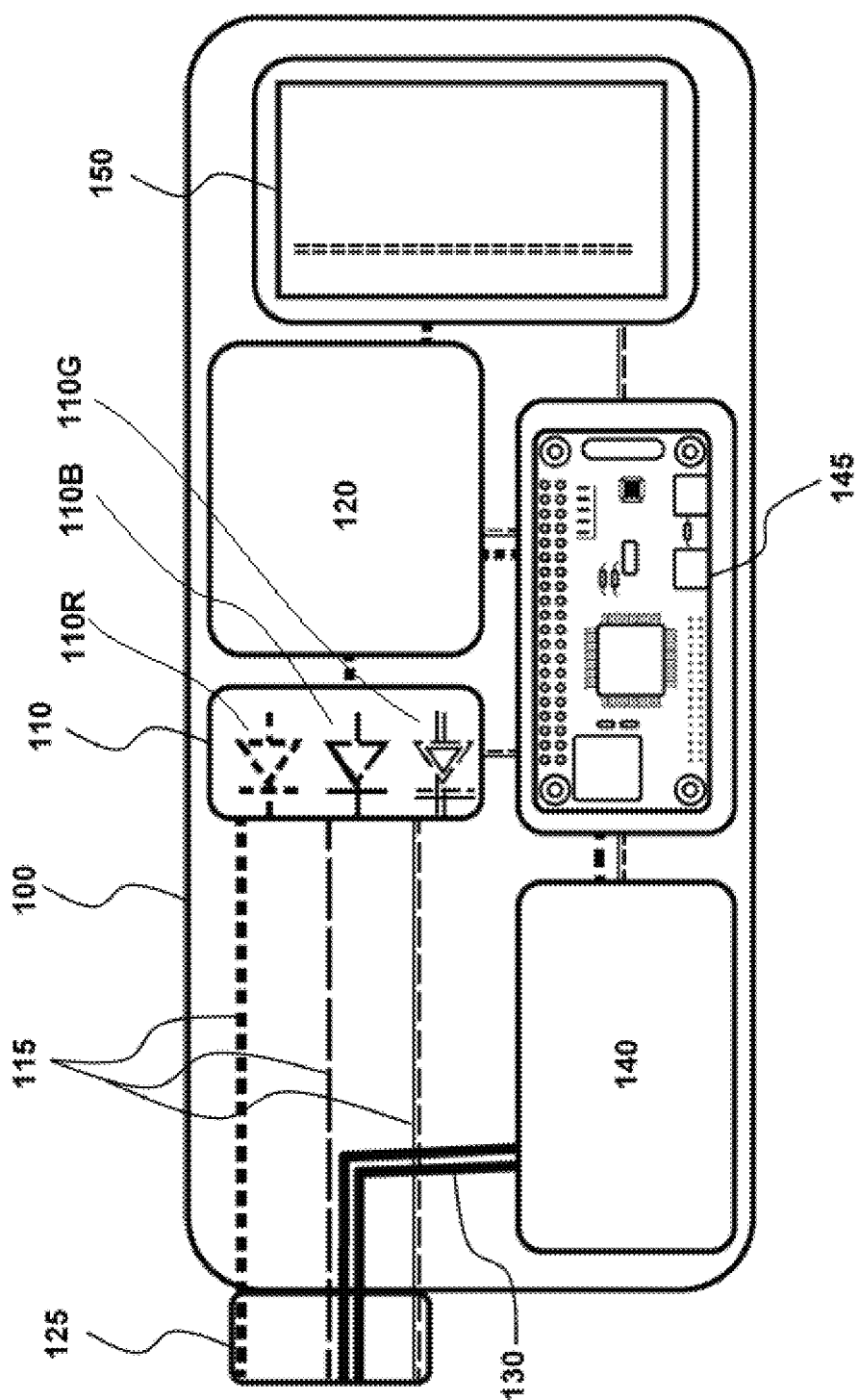
FIG. 1 is schematic block diagram of a light-based sensor configured to excite, measure, and analyze laser fluorescence spectra, in accordance with some embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the fields of fluorescence spectroscopy, medical-device engineering, and machine/deep learning. Indeed, the inventors wish to emphasize the difficulty of recognizing those problems that are nascent and will become much more apparent in the future should trends in industry continue as the inventors expect, particularly those problems that span different fields of study, like machine/deep learning and fluorescence spectroscopy Further, because multiple problems are addressed, it should be understood that some embodiments are problem-specific, and not all embodiments address every problem with traditional systems described herein or provide every benefit described herein. That said, improvements that solve various permutations of these problems are described below.

The current standard of care for skin cancer screening is a visual inspection by primary care physicians or dermatologists, by the naked eye or using a dermascope. Visual inspection typically heavily relies on medical experience, which can be expensive, slow, subjective, and less accurate than is desirable.

It is believed that doctors would benefit from data from fluorescence measurements. These measurements illuminate tissue, thereby causing the tissue to fluoresce, and sense properties of the resulting light. The measurements are expected to provide information about the relative contents of endogenous tissue fluorophores, such as collagen, keratin, elastin, carotene and lipopigments, porphyrins, and nicotinamide adenine dinucleotide.

Problems exist, however, with many approaches to visually or programmatically classify tissue based on spectral features of the collected (or otherwise sensed) fluorescence. Often, visual techniques require extensive training of doctors and are again expensive and subjective. And many programmatic approaches are not well suited for the relatively high-dimensional data produced by scans, which can include hundreds or thousands of measurements of light intensity at different wavelengths. Engineering features to which models respond can be problematic, as often analysts fail to capture subtle interactions in the data, and the features can prove brittle in the face of novel data. Indeed, classifying tissues based on spectral features of sensed fluorescence is challenging with many computer-based approaches. The spectral features of the collected spectrum can be significantly distorted, making the extraction of tissue biochemical composition from the measured signal difficult. (None of which is to suggest that any of these techniques or any other approach is disclaimed or disavowed, as the present techniques can be used in combination with other approaches, for instance, some embodiments combine visual inspection and engineered features with some of the techniques discussed below.)

Some embodiments apply artificial intelligence to sensed fluorescence spectra to assist medical practitioners. Some embodiments use deep learning to facilitate and enhance medical analysis. Embodiments capable of providing real-time accurate non-invasive sensing of the chemical constituents in biological tissues that could be applied in vivo, or in other materials and surfaces, are expected to be particularly desirable and beneficial. (Again, which is not to suggest that embodiments are limited to systems affording all of these benefits or implementing all of these techniques, as various cost and engineering tradeoffs may warrant different choices that would still be self-evident to an artisan given the benefit of this disclosure.)

For instance, non-invasive or minimally-invasive optical measurement approaches may be effectively carried out on certain tissues with the aim of providing an onsite, real time, in vivo characterization of the tissues. The application of optical imaging methods, as opposed to regular biopsies, supports a class of use cases in which tissue is not removed or modified in any way (for example, for histological analysis). Non-invasive optical approaches can solve many problems in diagnostics, though the claimed techniques can also be used with more invasive approaches as well.

Examples of optical imaging and related techniques, and some of their limitations, include: visual imaging (not accurate, gives only the shape and color of the objects), Holographic Imaging (not giving concentrations and composition information, cannot be applied in endoscopically); Absorption Spectroscopy (not accurate enough, only scalar intensity signal from one point, difficult to distinguish spectra from various substances); Raman spectrophotometry (not accurate enough, only scalar intensity signal from one point, difficult to distinguish spectra from various substances); Fluorescence Spectroscopy (not accurate enough, only scalar intensity signal from one point, difficult to distinguish spectra from various substances); Mass spectrometry (not-remote, the material/substance must be specially prepared, not real-time, unacceptable in-vivo); Ultrasound (low resolution, need to have a direct contact, does not give information about composition and concentration); X-Ray (harmful for using for medical purposes, gives information only from absorption coefficient); Magnetic Resonance Imaging (not real-time, not-remote, not fast, need to place an object to the magnetic field; not acceptable for metals); Positron Emission Tomography (not real-time, not-remote, not-fast, need to apply probe inside the scanning, not convenient for use for materials); Scintigraphy (not real-time, not-remote, not-fast, need to apply probe inside the scanning, not convenient for use for materials, and undesirable in virtue effects from probes used); and Electron Paramagnetic Resonance Imaging (not real-time, not-remote, not-fast, need to apply probe inside the scanning). Again, none of which is to suggest that any of these approaches are disclaimed, as data from the afore-mentioned techniques may serve as an additional channel of data that is paired with the output of models like those described below in an ensemble model that benefits from the strengths of different approaches.

The challenge of providing real-time, accurate, non-invasive or minimally-invasive sensing of the chemical constituents in biological tissues, liquids and materials that could be applied in vivo has not heretofore been satisfactorily solved. Some embodiments afford individual ones, or in some cases all, of these benefits or other benefits discussed below or that will be self-evident to readers in the relevant technical fields given the benefit of this disclosure.

In some embodiments, a device facilitating complex investigation of biological tissue may be implemented using laser fluorescence. Specific lasers/laser diodes with particular wavelengths may be integrated with optical and electronic units to procure and analyze information useful for rapid and reliable tissue characterization.

FIG. 1 illustrates an exemplary light-based sensor 100 (e.g., one including a fluorescence spectrometer for optical characterization of surfaces, sub-surfaces, and substances, such as biological tissues (e.g., of plants, animals, or humans). In some embodiments, the fluorescence spectroscopy system excites and measures fluorescence across 300 nm (nanometer) to 800 nm wavelengths. In some embodiments, three excitation light channels are measured (e.g. UV (ultraviolet), green and near infrared (NIR)). In some embodiments, two excitation light channels are measured. In some embodiments, an additional excitation channel is measured, e.g., in response to determining that the results from measured channels are not conclusive. In some embodiments, a measurement is repeated if the results are not in agreement with the results from the rest of the excitation light channels. In some embodiments, a user may choose how many excitation light channels are to be measured, and the illustrated device may respond to such inputs by effectuating the requested measurement. In some embodiments, a user may choose the wavelengths of the excitation light channels to be measured.

In some embodiments, the UV excitation light channels have a wavelength in the window of ~100-400 nm, the green excitation light channels have a wavelength in the window of ~500-600 nm, and the NIR excitation light channels have a wavelength in the window of ~650-900 nm. In some embodiments, the wavelengths of excitation light channels are at least 50 nm apart.

In some embodiments, the fluorescence spectroscopy device 100 may include three lasers/laser diodes 110; NIR laser 110R, green laser 11G and UV laser 11B. Each of lasers 110 may be a high-monochromatic light source, with tunable wavelength and intensity. In some embodiments, NIR laser 110R may emit a wavelength of around 632 nm; green laser 110G may emit a wavelength of around 532 nm; and UV laser 110B may emit a wavelength of around 365 nm. The outputs of lasers 110 may be conducted through extinction waveguides 115 to measuring head 125. In particular, in some embodiments, an extinction waveguide 115R conveys the output of laser 110R to measuring head 125; extinction waveguide 115G conveys the output of laser 110G to measuring head 125; and extinction waveguide 115B conveys the output of laser 110B to measuring head 125.

In some embodiments, the measuring head 125 may touch the skin directly to perform the measurement. In some other embodiments, a contact medium may be applied on the skin before placing the measuring head 125 on the skin. The contact medium may be a gel, a cream or a solution to ease the movement of the measuring head 125 or reduce the noise by providing a homogenous medium between the measuring head 125 and the skin. The contact medium may have little to no adsorption (e.g. less than 10%, like less than 1% of the light energy for a 1 mm thick film) in the wavelength of the lasers.

In some embodiments, the measuring head may be kept at the vicinity of skin (e.g. a few millimeters, like closer or further than 1 mm, 5 mm, or 10 mm), without directly touching the skin. Any applied pressure on the skin may affect the circulation of the blood and therefore change the fluorescence excitation spectra, though some use cases may also apply such pressure.

In some embodiments, the measuring head may be kept parallel to (e.g., within 20 degrees of, like within 10 or 5 degrees of) the normal vector of the surface skin being measured to provide maximum penetration. In some embodiments, the measuring head may be kept with an angle less than 45 degrees from the normal of the skin.

In some embodiments, the measuring head may terminate in, be part of, or otherwise be optically coupled to an endoscope (e.g., with an optical bundle that extends between the light sources/sensors and the head to convey stimulant light and return fluoresced light to the light-based sensor 100), and some embodiments apply similar measurements to internal tissues. For example, some embodiments may sense compounds indicative of, or classify tissues as having or not having lung cancer, bladder cancer, oral cancer, or thyroid cancer.

Figure 2:
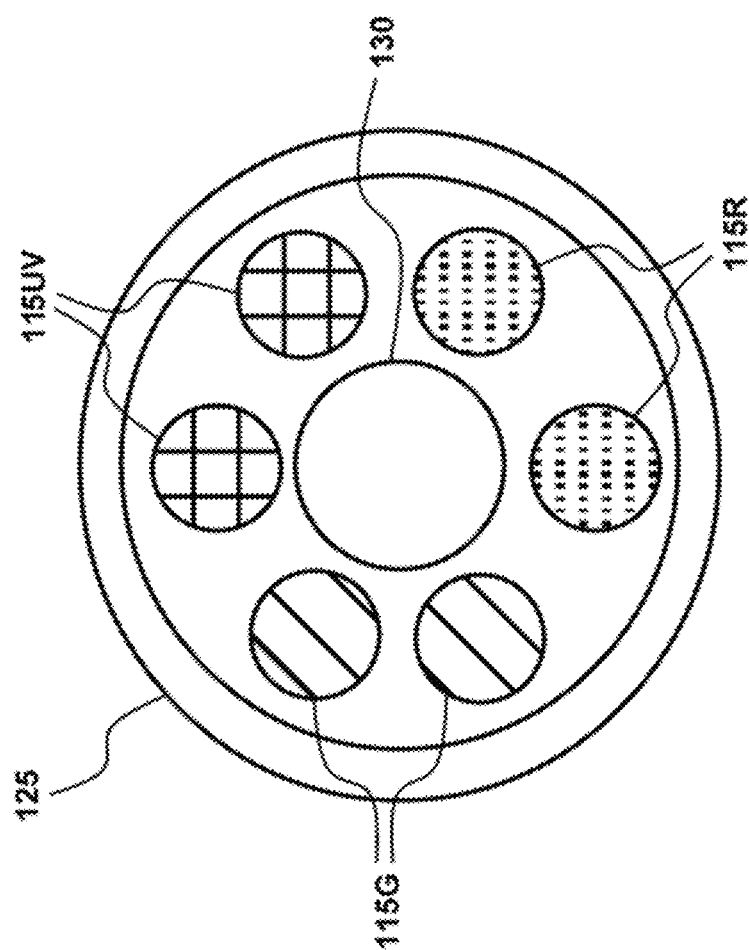
FIG. 2 is an end view of an embodiment of a measuring head of the light-based sensor of FIG. 1, in accordance with some embodiments.

FIG. 2 illustrates an exemplary embodiment of measuring head 125 from an end view (i.e., the view facing the skin or other tissue being measured), looking coaxially with the output of extinction waveguides 115G, 115UV, and 115R. Measuring head 125 may include output ends of laser waveguides 115G, 115R and 115B. In some embodiments, one, two, or three collecting fibers may be provided for each channel. In some embodiments, all the fibers are parallel to each other. In some embodiments, fibers may not be parallel to each other, in some embodiments, fibers for channels with the same wavelength may be parallel to each other or may be not parallel. The fibers may be arranged circumferentially around a central spectrometer waveguide 130. This arrangement is expected to provide for a high level of signaling collection by a physically compact (e.g., relatively small diameter, like less than 5 cm, like less than 3 cm, or less than 1 cm) optical probe measuring head 125. In some embodiments, a back-up spectrometer waveguide may be provided to acquire duplicates.

Return energy from the tissue (e.g., fluorescence) may be conducted via spectrometer waveguide 130 to spectrometer 140 (shown in FIG. 1) for evaluation and measurement. In some embodiments, spectrometer waveguide 130 may be located in the middle of the fibers to receive a relatively strong signal emitted from the tissue. In some embodiments, the spectrometer waveguide 130 may be located in a separate measuring head, different from the head with laser waveguide fibers. In some embodiments, the spectrometer waveguide 130 is located adjacent to the fibers to receive high level fluorescence signal being emitted from the tissue. In some embodiments, the spectrometer waveguide 130 may be positioned parallel to the laser waveguides fibers or with some angle (e.g., within a 30-degree angle) with regards to the laser waveguides fibers. In some cases, different extinction waveguides may be paired with different spectrometer waveguides positioned to sense their different effects on the tissue.

In some embodiments, lasers are activated sequentially, one-by-one and the lasers with the same wavelength provide duplicates to assess reproducibility and accuracy (though some embodiments may include only one of each color or some embodiments may multiplex waveguides with multiple colors down the same waveguide, which is not to suggest that other described features are not also amenable to variation). In some embodiments, the lasers with the same wavelength are activated at the same time to provide stronger signals. In some embodiments, only output fibers with specific wavelength are activated depending on the type of skin being examined and the purpose of the examination based on the input instructions by a user. In some embodiments, some of the wavelengths may be preferred over others based on the accuracy of the detection based on the difference of the intensity between normal tissue, mole, and cancerous tissue spectra.

In some embodiments, the lasers are activated one-by-one, after each other. In some embodiments, the lasers are activated all at the same time, or during overlapping durations of time. Each of the lasers may be on for 0.1, 0.5, 1, 3, or 10 seconds. The lasers may be activated multiple times each at the same or different intensity. In some cases, each laser (e.g., laser diode) may have the same duty cycle, or duty cycles may vary.

In some embodiments, measurements of the skin may be based on the interactions of nonionizing electromagnetic radiation and the skin. The absorbed energy may be dissipated as heat (tissue absorption), reemitted as electromagnetic radiation of lower energy with a longer wavelength (fluorescence), or even reemitted as radiation of higher energy (Raman scattering). The spectrometer may separate the returned light into individual wavelengths (or filter for different wavelengths at different times) and assesses it. In some embodiments, the intensity of individual wavelengths are measured for assessment. The intensity of individual wavelengths may be an average (or other measure of central tendency) intensity over time, average intensity received from different lasers, or a combination of both. The individual wavelengths may be 1 nm, 2 nm, 5 nm, or 10 nm apart (or more or less than these values) from each other. In some embodiments, sampling frequency may be determined based on input instructions received by the device from a user via a user interface of the device, like buttons, a touchscreen, audio input, or the like.

In some embodiments, the depth to which radiation penetrates the skin determines the depth from which information can be obtained. Penetration depth may be limited by the attenuation of light due to absorption and scattering. The penetration depth of light into the skin is expected to be about 1 mm at the red end of the visible spectrum (e.g. around 700 nm, for certain light intensities) and it is expected to decrease by approximately an order of magnitude around the blue end (e.g. around 400 nm). It further decreases between 400 and 300 nm. In some embodiments, around 700 nm information may be obtained about all skin layers, but below 290 nm the effective penetration depth is limited to the epidermis.

In some embodiments, the device may interrogate tissue components at the surface and at certain depths within the tissue by changing the excitation and emission wavelengths accordingly. For example, by changing from blue laser (e.g. 400-500 nm) to green laser (e.g. 500-540 nm) wavelength light, excitation of deeper tissue/bacterial fluorescent sources may be achieved. In some embodiments, multiple different intensities at different wavelengths may be measured to assess tissue at different depths.

In some embodiments, a double monochromator may be used to improve the signal to noise ratio at short wavelengths (e.g. below 400 nm). The two monochromators may be connected in series, with their mechanical systems operating in tandem so that they both select the same color. This arrangement may not be intended to improve the narrowness of the spectrum, but rather to lower the cutoff level. Each of the monochromator may be a prism or diffraction grating. In some embodiments, one monochromator is used to select the excitation wavelength and a second monochromator is used to analyze the emitted light. The monochromators may be used to analyze the light coming from the tissue. Some embodiments may include a polychromator integrated with a reflection grating and a CMOS (complementary metal oxide semiconductor) linear image sensor.

Figure 10:
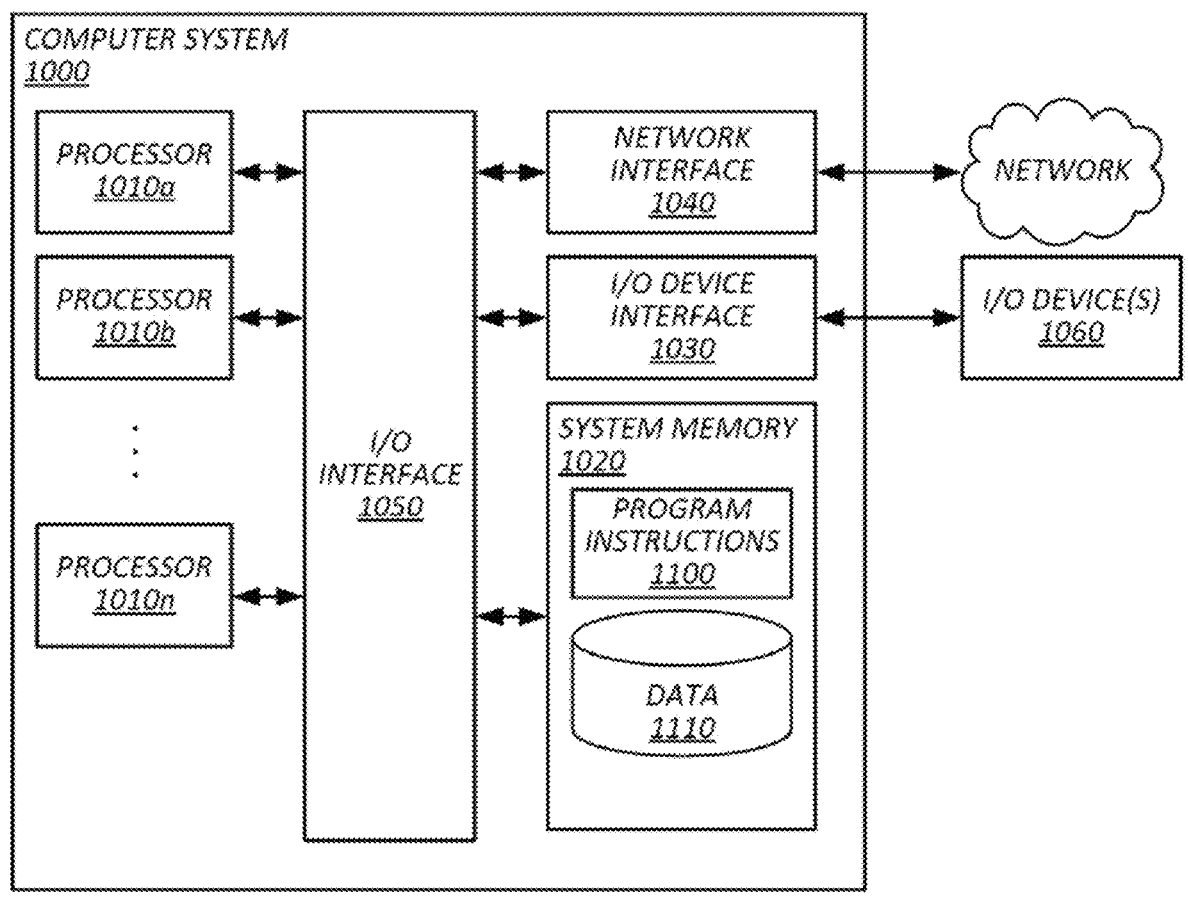
FIG. 10 is a diagram that illustrates an exemplary computing system by which some of the present technique may be implemented.

Output of spectrometer 140 may be communicated to microcomputer 145 (e.g., an embedded microcontroller, or a computer like that described below with reference to FIG. 10), and make take the form of a distributed computing architecture or a monolithic computing architecture. In some embodiments, microcomputer 145 may implement integrated neural networking architectures (or other models discussed below), and may include dedicated processors to facilitate efficient implementation of neural network functionality, like an AI-inference hardware co-processor. In some embodiments, a microprocessor, an application-specific integrated circuit, a digital memory chips, complex programmable logic device, or a field-programmable gate array may be used to integrate the neural networking functionality.

Microcomputer 145 may drive display screen 150, such as a touchscreen, or displays may be effectuated on other devices, like another computer, such as a smartphone executing a native application configured to communicate with the device 100 to display results and enter commands. In some embodiments, microcomputer 145 may be provided with alternative or additional output modalities, including, without limitation (which is not to suggest that other descriptions are limiting), cable-based output to another device providing user interface functionality, and/or an API (application program interface) or other digital or analog interface for communications to and from other devices.

All of the aforementioned components may be powered by an AC/DC power supply, a compact battery bank, or a rechargeable battery pack, for example, in some embodiments. In some embodiments, the device may be adapted for connecting to an external power supply. In some embodiments, fluorescence spectroscopy device 100 may be implemented in a compact physical package, such as one having a length of about 140 mm (or less) and a width or height of about 60 mm (or less), e.g., some embodiments may occupy a volume of less than 1,000 cubic centimeters). In some embodiments, fluorescence spectroscopy device 100 may be implemented in a hand-held, or a wearable physical format. In some embodiments, fluorescence spectroscopy device 100 may be in one piece, or multiple segments connected to each other via wires, or wireless means (e.g. Wi-Fi). In some embodiments, fluorescence spectroscopy device 100 may be implemented in a portable package that may be connect to smart phones, wearable head-mounted-display computing devices (like augmented reality displays that overlay the doctor's view of the patient with outputs like those described below, in some cases with outputs overlaid on the part of the patient to which they apply), or other computers to perform the diagnosis.

Fluorescence spectroscopy device 100 may also include a beam line scan generator for space scanning or a multi-axis robotic arm to move the device 100 through a scan path, like described below with reference to FIG. 8. In operation, fluorescence spectroscopy device 100 may be used to apply various optical outputs to a subject's biological tissue, measure responsive return signals, and then process those return signals to provide characterization or evaluation of the subject's tissue. For instance, the laser and extinction intensity may be selected by microcomputer 145. While exposing a sample to the laser signal, the fluorescent response comes from measuring head 125, through spectrometer waveguide 130 to spectrometer 140. In some embodiments, spectrometer 140 transforms optical signals to digital signals, which are then passed to microcomputer 145 for processing. After a spectrum is stored by microcomputer 145 for a given input (e.g., a particular laser and voltage), a subsequent laser and voltage may be selected to produce the next spectrum for application to the same object, in some cases.

As a result, in some embodiments, microcomputer 145 may store an analysis result in the form of a multidimensional array in memory. For each tuple of angles (thi, theta) that is generated by the scan generator and corresponds to the [X,Y] coordinates of the scanning sample, a fluorescence spectrum may be generated, extincted by all wavelengths from the range L1=[Lhigh . . . Llow] and the intensity range I [Ihigh . . . Ilow]. Therefore, in sum, the output "image" may be a 6-D tensor with the following axes: (1) Thi-angle (corresponds to X-coordinate); (2) Theta-angle (corresponds to Y-coordinate); (3) L1—extinction wavelengths; (4) I—intensity of extinction radiation, (5) L2—scanning wavelength be spectrometer; and (6) Timestamp. In some cases, additional fields may indicate device pose relative to the patent (e.g., with six coordinates indicative of position and orientation or fewer coordinates), when device pose is varied throughout a scan, or when a spatial array of scanners is positioned to image different adjacent regions of the patient. Data need not be labeled as embodying these constructs to serve as such in program code, provided the corresponding information is encoded.

With regard to wavelengths, some embodiments may implement processes that occur at wavelengths in the 300-980 nm range, spanning the ultraviolet (UV), visible and NIR regions of the spectrum. In this range, the electronic structure of matter may be most relevant, since electrons predominantly interact with these electromagnetic waves. The light penetration depth increases when moving from UV radiation to the NIR range. In some embodiments, wavelengths may be in second NIR window (i.e. 800 nm-1200 nm).

The 6D-tensor output cannot be observed visually because of its six-dimensional nature, but such high-dimensional tensors are amenable as input for various kinds of machine learning models, like deep learning neural networks, including multilevel neural networks with or without convolutional layers and with or without directed cycles of connections between perceptrons. Other examples include Bayesian neural networks (e.g., approximated with Markov Chain Monte Carlo), recurrent neural networks, reinforcement learning models, and decision trees (like random forests thereof). The output of these networks could also be interpreted as a regression problem (e.g. to retrieve the concentrations of substances), and/or a multi-classification problem (e.g. to retrieve the composition of substances, or time-related dynamics given by recurrent neural network architectures, like long-short term memory models, or various transformer architectures with attention). Moreover, multiple such approaches may be combined (such as combinations of regression, classification and time-related prediction). The output of the neural network engine within microcomputer 145 may be stored in memory and shown in display 150 and/or communicated through external interface (e.g. a wired monitor or a wirelessly accessible computing device with a screen).

Some combinations of data that may be acquired optically and noninvasively by fluorescence spectroscopy device 100 have been determined to be particularly effective as inputs to classification and characterization approaches relying upon machine learning techniques, for a wide variety of clinical, medical or industrial applications. For example, in some embodiments, measuring head 125 of fluorescence spectroscopy device 100 may be applied against a section of human skin, with the resulting tensor output of spectrometer 140 utilized as input to a deep learning neural network, which may then be trained using such inputs to rapidly characterize and classify skin cancer within the observed section of skin at a level of accuracy comparable to typical expert doctors.

Model selection may depend on various criteria, like training sample size, whether interpretability of the model is required, and whether the objective function used to train the model is differentiable. For example, Bayesian optimization may be used for non-differentiable objective functions. In some embodiments, the resulting tensor output of spectrometer 140 utilized as input to a Markov chain Monte Carlo (MCMC) algorithm. A MCMC simulation may be used to stochastically select the subset of data patterns corresponding to dominant conditional bit probability terms (e.g. excitation fluorescence spectrum) in the channel data bit probability summation. By summing a subset of data patterns corresponding to the dominant terms, rather than summing over all possible data values, a significant reduction in the processing can be obtained relative to an exact calculation of the channel data bit probability summation. In some embodiments, a number of simulations may be run in parallel. Such an approach may also prove useful when available processing speed is a practical limitation. Moreover, the samples drawn in successive iterations from a single Markov chain are correlated. In contrast, the parallel simulations draw a pool of samples which are less correlated; generally only the samples that belong to the same Markov chain are correlated. Additional examples of contemplated models, like decision trees, autoencoders, and various ensemble models, are described below with reference to FIG. 9.

In some embodiments, the results of the fluorescence measurement is pre-processed (e.g., before input the model) to reduce the artefacts. Reference to emission data, including in the form of a matrix, should be read generally to refer to both the raw data and transformations thereof before input to the mode (e.g., reference to "the excitation-emission matrix" maps onto any one and each of these various different states in a pre-processing pipeline, notwithstanding use of the definite article, so "obtaining the matrix" and "inputting the matrix to a model" encompasses scenarios in which the matrix is modified with pre-processing after being obtained and before being input to the model.) To overcome the artefacts, such as presence of hair and obstruction of the laser light, mean, median, Gaussian and anisotropic filters may be employed to increase the accuracy of the results. In some embodiments, multiple measurements are performed in one area and the artefacts may be filtered out before being processed by a deep learning neural network. In some cases, the model may be responsive to some hand-engineered features that are also computed during pre-processing.

In some embodiments, pre-processing may be used to reduce patient-to-patient variations in intensity, while preserving inter-category differences. Such pre-processing may include normalizing each emission spectrum to its respective maximum intensity, filtering outliers, and applying various filters.

Some embodiments apply machine-learning techniques to learn from previous inputs (e.g., in a batch process, or with active learning) without being explicitly programmed to minimize the occurrence of false results and predict type of the tissue (e.g. cancerous tissue or normal tissue) with high accuracy. Some embodiments afford machine-learning systems that implement Bayesian statistics, a branch of mathematics that employs "degrees of belief" to interpretations of probability, to create algorithms that make predictions on data. Some embodiments identify patterns of working across multiple (e.g., 2 or more, 3 or more, 5 or more, 10 or more, or 40 or more) variables to predict the type of tissue. By looking back at previous measurements and results, and applying the lessons learned, the system can speed up tissue assessment process. Trawling through a database of logged events for a description that matches the issue at hand, the system can provide accurate assessment in real-time to provide a helpful guide for the type of tissue being examined.

In an exemplary study, an embodiment of fluorescence spectroscopy device 100 was used to classify skin tissue types as "normal tissue," "mole," or "cancer," based on luminescence (e.g., fluorescence) spectra. Raw data was luminescence spectra from tissue with three different sources of laser extinction. The spectrum resolution was 1 nm and the measurement limits were from 100 nm to 2100 nm. Thus, 2100×3=6300 data points were collected for each instance.

Normal fluorescence spectra were collected from different skin areas of a number of healthy individuals using a device such as fluorescence spectroscopy device 100. Oncologic patients were also examined, with fluorescence spectra collected from the center of the visible area of a presented cancer, from three to five points around the visible center of the tumor, and additionally from the normal (intact) soft tissue next to the cancerous area. Around 300 patients with different skin, head and neck cancers were examined before, during and after radiotherapy course of treatment and around 50 health volunteers.

In some embodiments, excitation spectra are acquired because these also provide information on the absorption properties of the chromophores. In some embodiments, emission spectra are acquired.

Some embodiments of the present disclosure may be used in screening for cancer in skin or other tissues, such as the lung tissue (e.g. gastrointestinal lining epithelial tissue). The method of the present disclosure may be used in vivo or in vitro depending on the type of tissue being screened.

Figure 3:
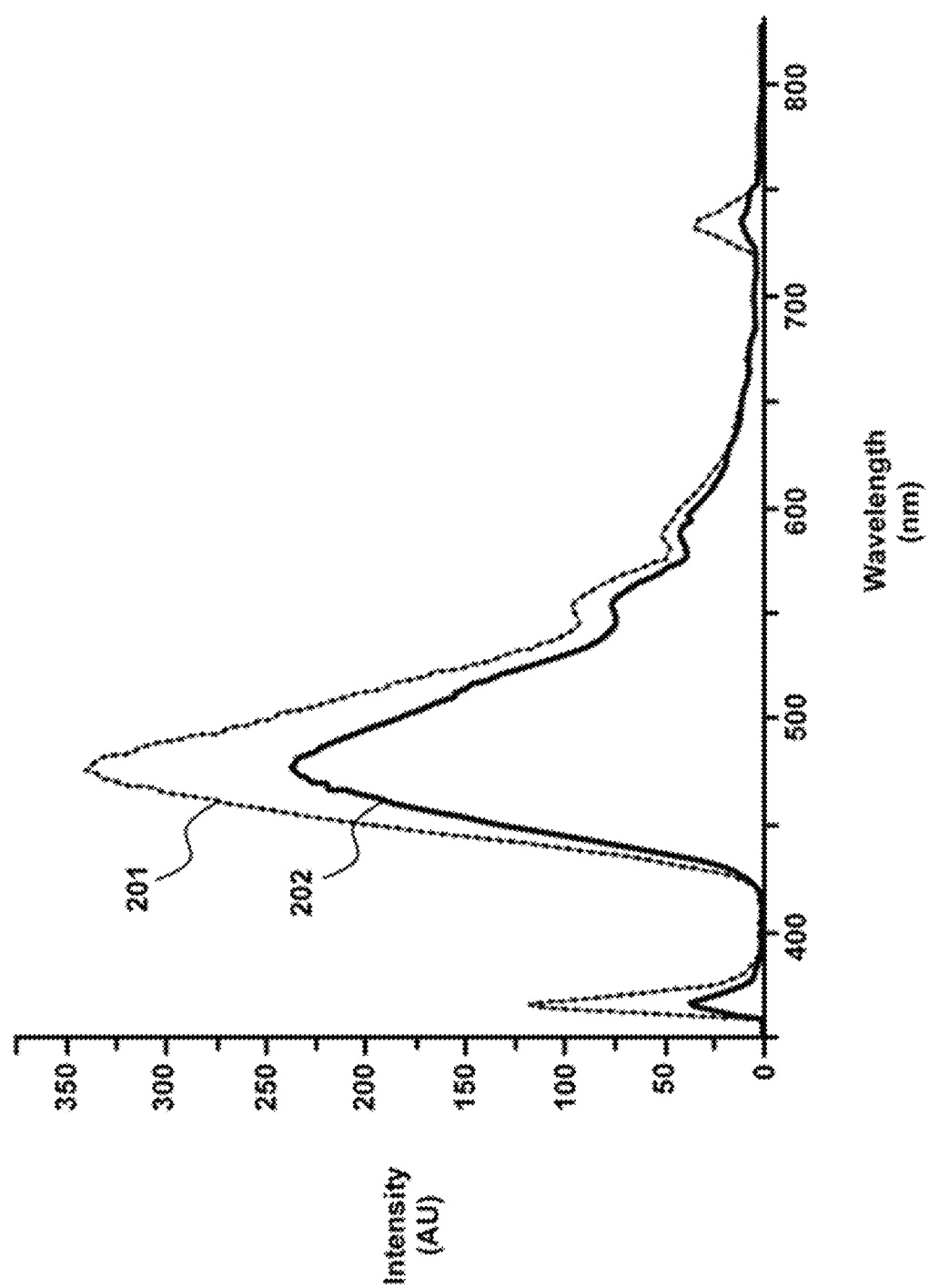
FIG. 3 is a plot of fluorescence intensity measurements for excitation of normal and cancerous skin cells using a 365 nm laser measured with the light-based sensor of FIG. 1, in accordance with some embodiments.

FIG. 3 illustrates exemplary fluorescence measurements for excitation of normal 201 and cancerous 202 tissues by a 365 nm laser/laser diode (i.e., UV laser 110B, in some embodiments). As can be seen, while both normal tissue, and cancerous tissue have peaks at similar wavelengths, the intensity of the peaks related to cancerous tissue is less than that of normal tissue.

Figure 4:
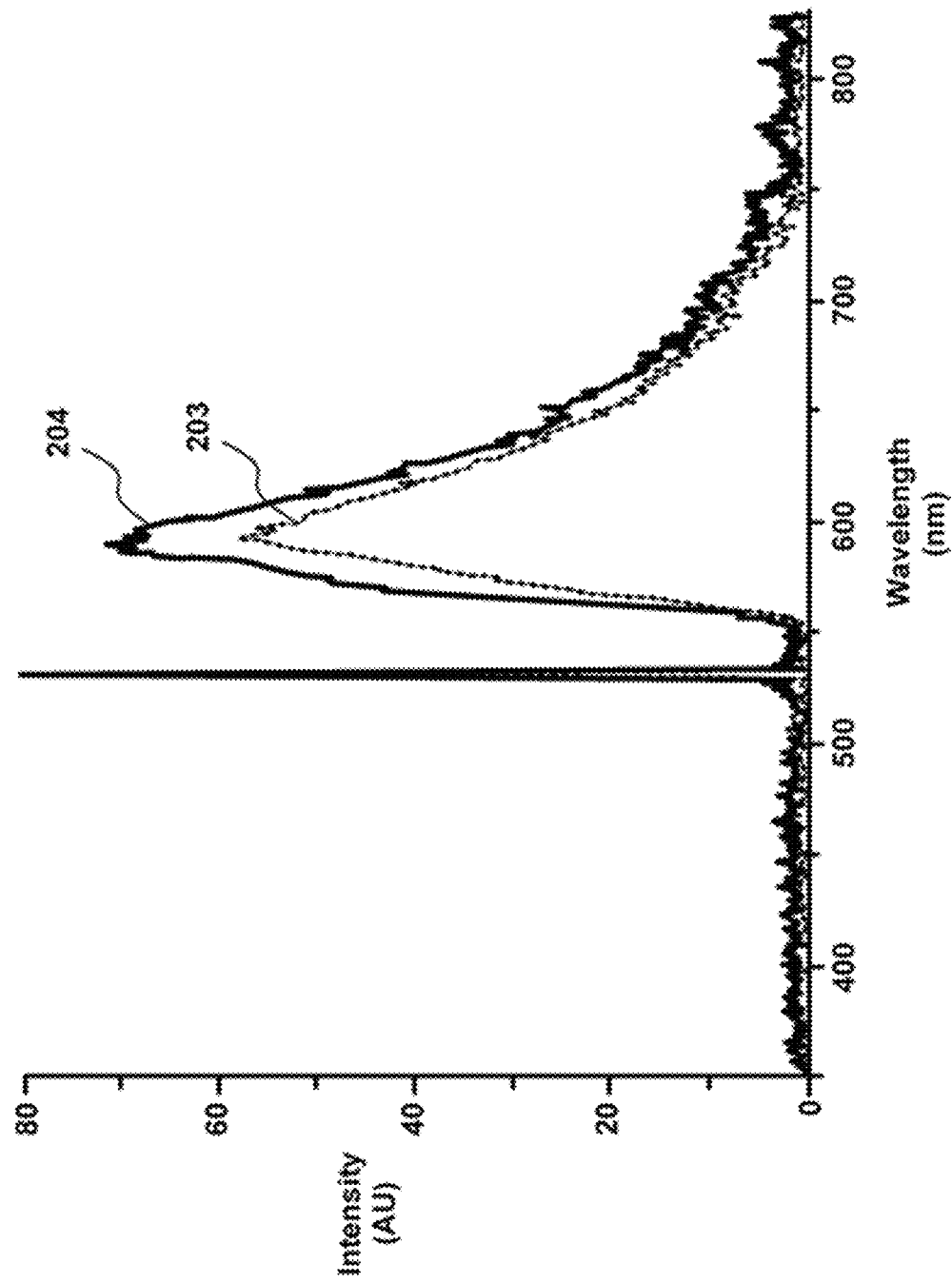
FIG. 4 is a plot of fluorescence intensity measurements for excitation of normal and cancerous skin cells using a 532 nm laser measured with the light-based sensor of FIG. 1, in accordance with some embodiments.

FIG. 4 illustrates exemplary fluorescence measurements for excitation of normal 203 and cancerous tissues 204 using a green 532 nm laser/laser diode (i.e., laser 110G, in some embodiments). In contrast to the results obtained from UV laser, the intensity of the cancerous tissue in green laser is higher than that of normal tissue. However, the location of the peaks in green laser spectra for both cancerous tissue and the normal tissue are at almost the same wavelengths.

Figure 5:
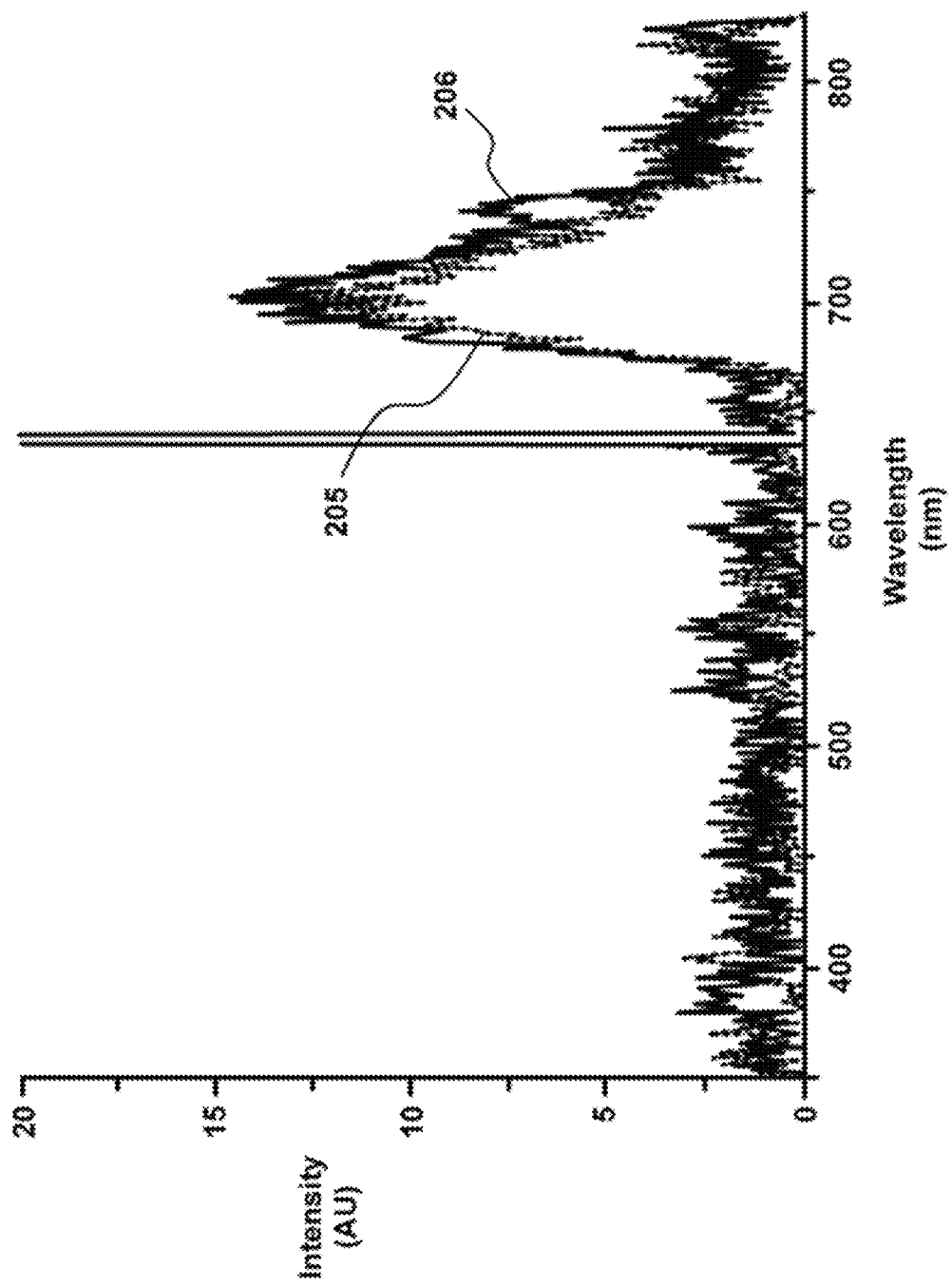
FIG. 5 is a plot of fluorescence intensity measurements for excitation of normal and cancerous skin cells using a 632 nm laser measured with the light-based sensor of FIG. 1, in accordance with some embodiments.

FIG. 5 illustrates exemplary fluorescence measurements for excitation of normal 205 and cancerous 206 tissues using a NIR 632 nm laser/laser diode (i.e. laser 110R, in some embodiments). The spectra of cancerous tissue is located above the normal tissue while the wavelengths of the peaks are almost the same.

Figure 6:
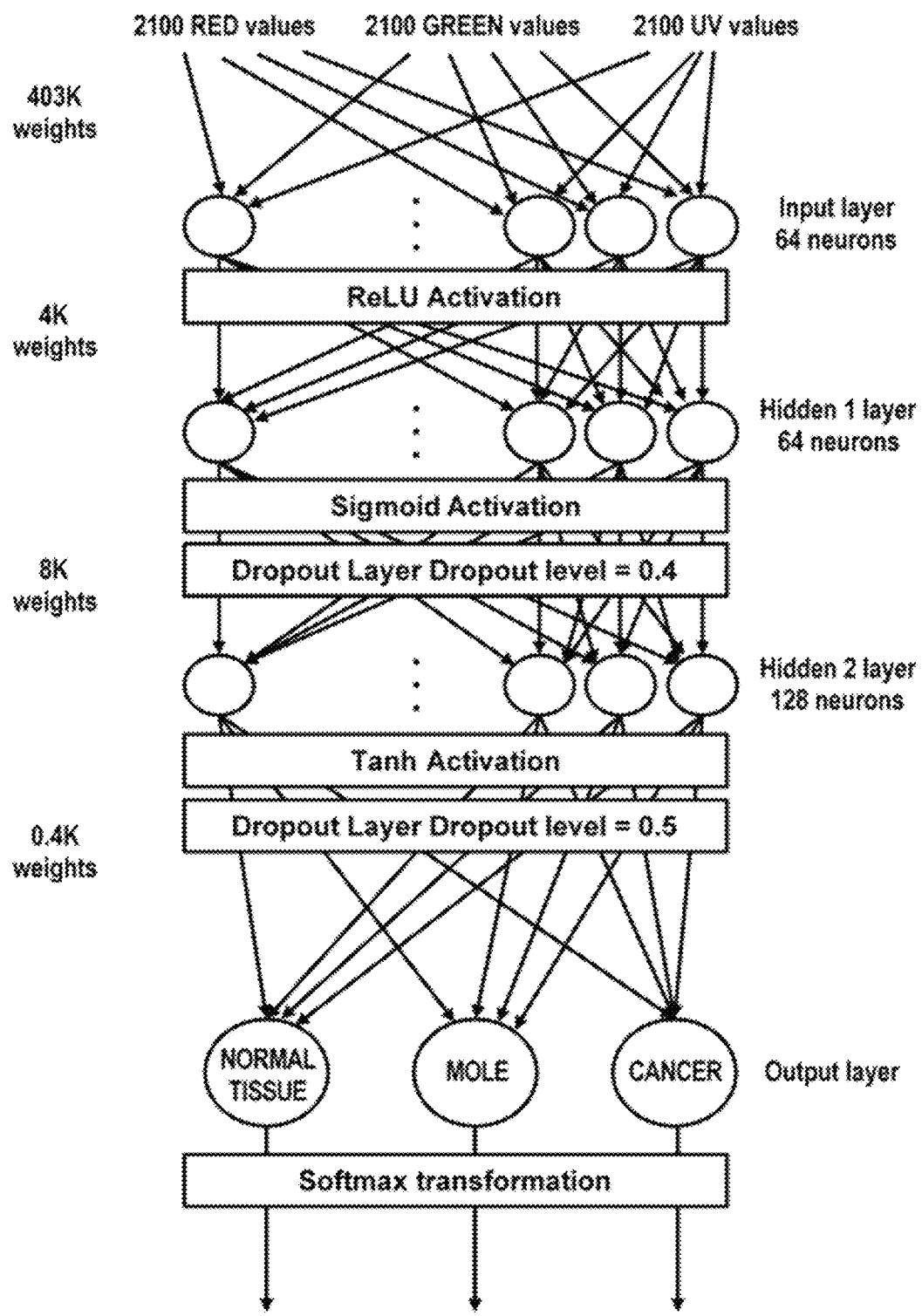
FIG. 6 is schematic diagram of a model architecture of a neural network receiving laser fluorescence spectra and outputting a surface classification, in accordance with some embodiments.

Measured spectra were applied to a dense neural network implemented by microcomputer 145, having the network architecture illustrated in FIG. 6. Four layers are provided in this example: an input layer, two hidden layers, and an output layer. Layer 1, in this embodiment, is a dense layer, with 64 neurons, ReLU activation, and no dropout. Layer 2, in this embodiment, is a dense layer, with 64 neurons, Sigmoid activation, and 0.4 dropout. Layer 3, in this embodiment, is a dense layer, with 128 neurons, Tanh activation, and 0.5 dropout. Finally, the output layer, in this embodiment, has 3 neurons (corresponding to classifications of "normal tissue", "mole" and "cancer"), with Softmax output transformation. The total number of fitting parameters is therefore 416,131, including various weights and biases associated with each neural and connections therebetween illustrated by the architecture of FIG. 6, in which outputs of some neurons serve as inputs to others. Microcomputer 145 includes an edge Tensor Processing Unit (or other hardware accelerator for machine learning inference) to provide faster fitting, though other hardware accelerators are contemplated and discussed below with reference to FIG. 9. The output can be expressed as classification probabilities for each of the three potential classifications.

Training was conducted on a sample of 106 examples. Classifier effectiveness was then validated on independent samples. For all of the samples, the device was able to recognize tissue type with an accuracy level of 99.8%, with a type I error rate of 0.2.

Figure 7:
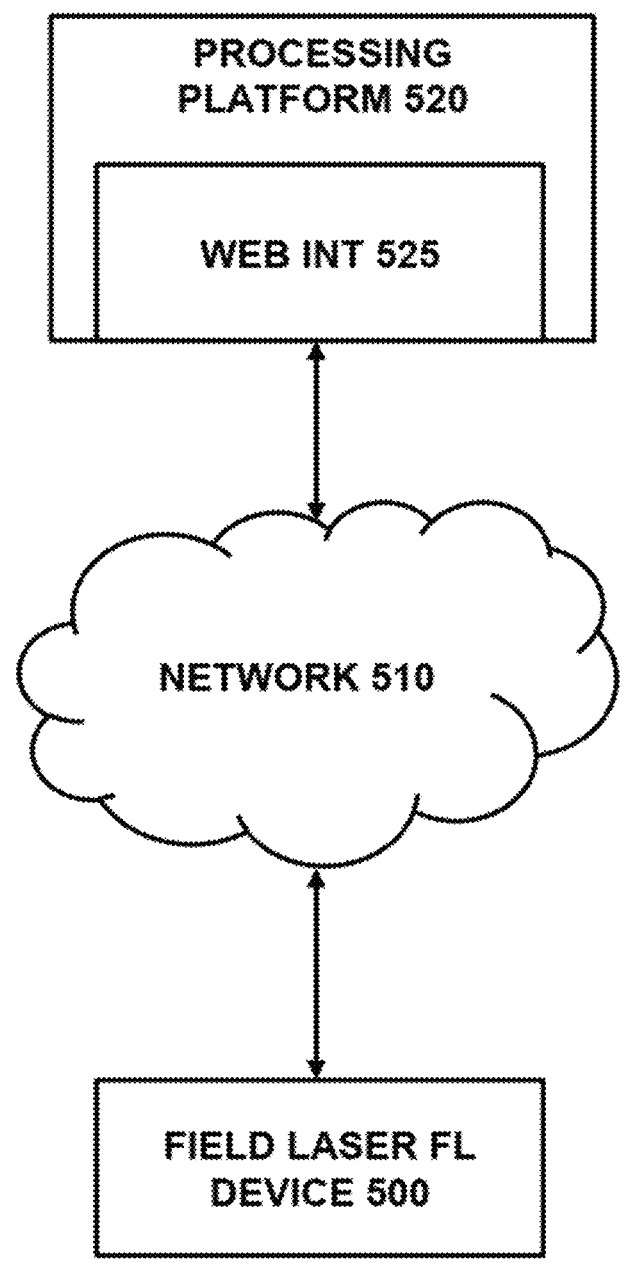
FIG. 7 is a schematic block diagram of a light-based sensor communicating with a remote processing platform, in accordance with some embodiments.

While FIG. 1 illustrates an integrated device, in which a microcomputer with neural network implementation is fully integrated with hardware components for laser excitation and measurement of resulting fluorescence spectra, it is contemplated and understood that in other embodiments, alternative architectures may be provided with different distributions of components and functionality, which is not to suggest that other aspects are limited to the arrangement depicted or described. For example, FIG. 7 illustrates an embodiment in which a field device 500 may be provided with the laser/optical emission and fluorescence measurement components of fluorescence spectroscopy device 100, but in which fluorescence spectra data is stored locally. Such spectra may then be transmitted via data network 510 (which may include the Internet) to remote network-connected computing platform 520, which may include web interface 525 to facilitate network-based interactions. Platform 520 may the implement a neural network such as that of FIG. 4, and/or expert systems or other mechanisms for processing the spectra collected by field device 500. Thus, platform 520 provides a centralized resource for analysis, classification, diagnosis, annotation or other processing and/or storage of patient fluorescence spectra. In some cases, additional computing devices may be part of the computing ecosystem. For instance, embodiments may interface with electronic medical record systems, like via the Fast Healthcare Interoperability Resources (FHIR) interface and schemas to update medical records with scan results and effectuate invoicing to insurance companies and patients.

While the apparatus and techniques described herein may be beneficially employed in clinical and medical contexts, it is contemplated and understood that the laser fluorescence data captured they may also be effectively used to feed neural networks for analysis and classification of many other surfaces and materials. Such applications include non-medical applications as well, such as industrial quality control monitoring of surfaces and components, and/or material testing. The methods and apparatuses described herein may be applied to real-time scanning in the processes of precise metal fabrication, in air/water quality analysis, and in precise chromatography in oil, gas and chemical industries. As yet another example, in the polypropylene extrusion process, it may be very important to control the physical and chemical parameters of the propylene/polypropylene mass and have the immediate feedback to control the pressure/temperature in parts of the extruder. A device such as fluorescence spectroscopy device 100 may be included as a controlling part of the extruder. In yet another example, in microscopic microbiology studies, a device such as fluorescence spectroscopy device 100 may be utilized to detect and separate special cells by using the proposed device as an additional microscope cap.

In some embodiments, light distributions within tissues is calculated via the Beer-Lambert law, the diffusion approximation and the Monte Carlo Radiation Transfer (MCRT) method. These mathematical approaches are based on radiative transfer equation to calculate the fluence rate. The fluence rate may be used to predict how the light will travel into target regions, such as tumors.

In some embodiments, information may be extracted as the tissue surface is imaged using fluorescence, which can identify precancerous and cancerous lesions, define lesion margins and guide localized treatment. Fluorescence differences observed between adjacent tissues provide a description about the biochemical state of the tissue and the changes associated with disease development.

In some embodiments, a fluorescence biochemical marker may be used. The fluorescence biochemical markers may improve the signal when compared with intrinsic autofluorescence signals. A fluorescence biochemical marker may be injected to the body in advance of fluorescence measurement to enhance the accuracy of the results by increasing the intensity of fluorescence emission. In some cases, genetic manipulation of a sample may be used to cause a living sample to produce such a marker, in some cases, conditional on various environmental or developmental conditions.

Some embodiments may augment the types of fluorescence-based inferences described herein with additional channels of information. In accordance with some of the embodiments of the disclosure, multiple images may be captured. The multiple images may be captured under different light source spectra or wavelengths. Multi-wavelength images with multiple different imaging modalities may be captured to perform the assessment through various methods. Fluorescence Imaging may be coupled with other imaging techniques such as Diffuse Reflectance Spectroscopy, Raman Spectroscopy, or Absorption Spectroscopy to provide more information regarding the tissue being examined. Multi-modal imaging may be performed with measuring heads similar to the one shown in FIG. 2 with having multiple types of laser lights suited for different imaging modalities. The images may be captured from the same angle or varying angles. One, two, three, four or more images may be captured. The images may be compared, contrasted, and/or overlaid.

In some embodiments, results of the analysis may be presented graphically in 2-D or 3-D charts. A database including a collection of measurements may be included in the representation.

Depending on embodiment, the visible light image and the emission spectra image may be presented interactively by the use of an operable slider that shows 100% of the visible light image at one end and 100% of the emission spectra image at the other end, with variable portions of each image overlaid for intermediate slider positions.

Depending on embodiment, the emission spectra image may be presented in a contrasting color overlaid with the visible light image. For example, fluorescence may show as bright green. Or it may be presented as a spectrum width radar and as hyperspectral imaging, also called imaging spectrometer. Or embodiments may use an image generated with ultrasound sensing or an imaging spectrometer.

In some embodiments, the fluorescence spectroscopy device 100 is hand-held or portable. In some embodiments, the device may also be embodied as not being hand-held or portable, for example as being attached to a mounting mechanism or coupled to other imaging modalities to perform multi-imaging modalities, concurrently.

In some embodiments, a method of classifying a tissue type (e.g. normal, cancerous, and mole) is provided. A database is prepared by collecting fluorescence spectra from different skin areas of a number of healthy individuals (e.g. more than 100 people) using a device such as fluorescence spectroscopy device 100. Oncologic patients (e.g., more than 100 patients) are also examined, with fluorescence spectra collected from the center of the visible area of a presented cancer, from three to five points around the visible center of the tumor, and additionally from the normal (intact) soft tissue next to the cancerous area. Machine-learning techniques may also be applied to learn from fluorescence spectra of normal tissue and cancerous tissue to compare the differences and minimize the occurrence of false results and predict type of the tissue (e.g. cancerous tissue or normal tissue) with high accuracy. Thereafter, a tissue type may be classified by illuminating the tissue with a plurality of light sources and obtaining, with a data processor, a set of fluorescence spectra from the emitted light. The artefacts may be filtered out and the spectra are normalized to maximum intensity. Using the trained model, the type of the tissue may be determined by comparing the fluorescence spectra to those stored in the database. The results may be stored in a memory and/or displayed on a monitor, in some embodiments.

In some embodiments, a score may also be calculated and assigned to represent the likelihood of a skin having specific characteristics analyzed by the software or a combined score of likelihood of a region of tissue being a skin cancer (e.g., melanoma) or a recommendation for a biopsy or a recommendation for additional evaluation. The score may be a numerical value along a scale that may provide chances of the detection of cancerous tissue. The score may be used to recommend one or more medical action, such as biopsy or additional evaluation.

In some embodiments, the fluorescence signal is deconvoluted to isolate the contribution of individual fluorophores to the apparent cumulative signal observed in the spectra. A score may be calculated by measuring the sensitivity of the device as a function of false negative rate. Age matched controls as the fluorescence of skin changes with age may be implemented. The fluorescence values obtained between the patients with the target condition and the age-matched controls may then be compared. Other control such as gender, race, and the like may be used depending on the disease to be detected or monitored.

Depending on embodiment, measurements, metrics and scores may be presented numerically or graphically.

Figure 8:
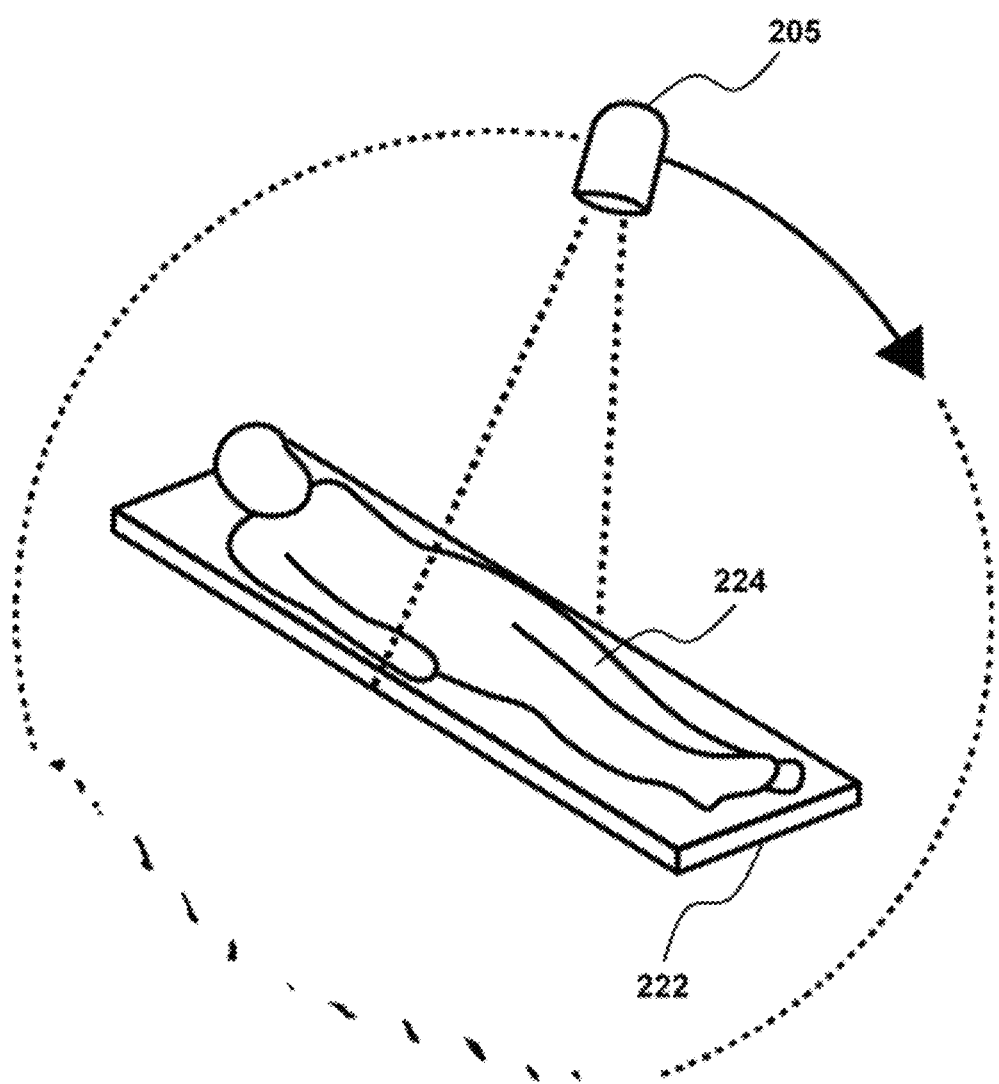
FIG. 8 is a perspective view of an example of a scanning light-based sensor, in accordance with some embodiments.

As shown in FIG. 8, some embodiments may scan a patient's body 224 with a light-based sensor 205 like those described above. A table 222 may move the patient along a path of travel and/or the device 205 may be moved to cause the scanned region to translate. Or some embodiments may include an array of devices 205 positioned to scan different regions around the patient as the patient is translated through the ring of scanners. Location information, like coordinates indicating relative pose, may be associated with inputs and outputs of the models described herein, e.g., to produce a map of the patient's body with scan results overlaid, like a heatmap where color indicates concentration or classification.

Figure 9:
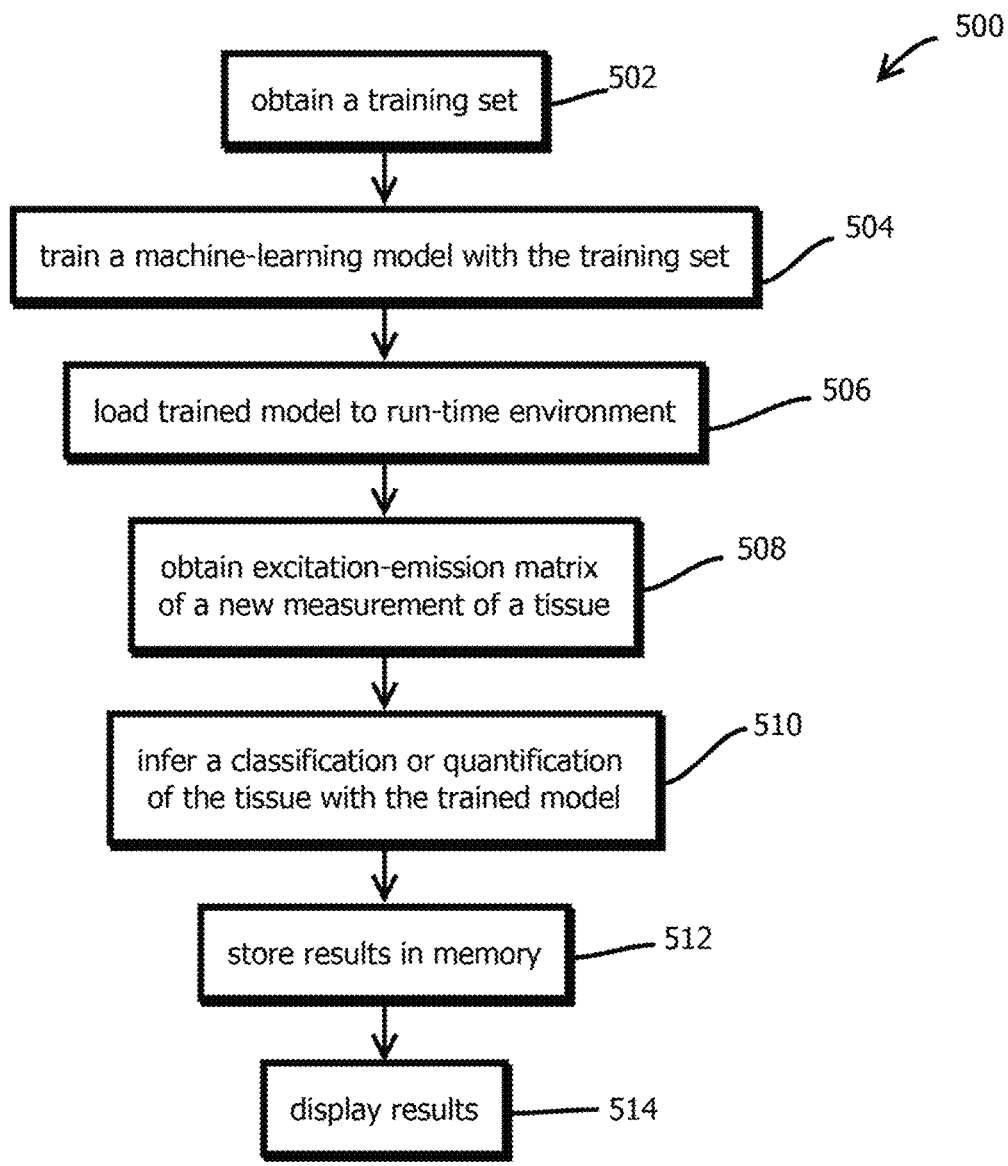
FIG. 9 is a flowchart depicting an example of a method of operating light-based sensors like those referenced above and other light-based sensors, in accordance with some embodiments.

Some embodiments may execute a process 500 shown in FIG. 9. In some embodiments, the process may be executed by one or more computing devices (like those described below with reference to FIG. 10 or shown above in FIG. 1) that are executing instructions embodying the process 500, those instructions being stored in one or more tangible, non-transitory, machine-readable media. In some embodiments, different computing devices may execute different subsets of the operations, as described below. Additional operations may be inserted, some operations may be omitted, operations may be repeated, operations may be executed sequentially or in a different order from that shown, and some operations may be executed concurrently, none of which is to suggest that any other description is limiting.

In some embodiments, the process 500 includes obtaining a training set, as indicated by block 502. In some embodiments, the training set includes a plurality of training samples, like more than or less than 50, 200, 400, 10,000, or 100,000 samples, with implications for optimal model architecture depending upon the size of the training set, as described below. For example, many off-the-shelf machine learning models presume training set sizes in the range of 10,000, and such architectures may not be well suited for use cases in which substantially smaller training sets are provided, as is often the case in medial use cases where expensive physician time is used to label data and privacy regulations prevent sharing of data. In some embodiments, each sample in the training set may characterize a different measurement of a different body of tissue with techniques like those described above. In some embodiments, each sample may be taken from a different patient, for example, or in some cases a given patient may supply multiple samples.

In some embodiments, each sample in the training set includes one or more excitation-emission matrices having fluorescence data like that described above. In some embodiments, each row of a given matrix may correspond to a wavelength of light by which a given tissue is illuminated (or range of wavelengths of light).

In some embodiments, each column may correspond to a wavelength of light at which the tissue fluorescence is measured for intensity. In some embodiments, each column may correspond to a range of wavelengths within which light intensity is sampled after the tissue is illuminated to stimulate fluorescent emission. In some embodiments, such wavelengths or ranges thereof may monotonically increase or decrease with column position, in some cases with each column position corresponding to a respective range having a width the same as other columns, or in some cases different columns may correspond to different ranges of sampled fluorescent spectra. In some embodiments, the difference between sampled wavelengths in each adjacent column may be approximately the same, or some embodiments may sampled different portions of the fluorescent spectra with different granularity, for instance, having wavelength step sizes of 10 nm for each column position near the edges of the matrix and 1 nm step sizes of sampled wavelengths for each column position near the middle columns of the matrix.

In some embodiments, column position corresponds to the same wavelength or range of wavelengths of emission spectra for each row, or some embodiments may index matrix positions into a table that indicates which emission wavelength each matrix position corresponds to, and some cases with different emission wavelengths or ranges thereof mapping to different rows in the same column (or in some cases such an arrangement may be characterized as a three-dimensional matrix, with a Z-index values indicating the emission wavelength corresponding to a row (X-index) and column (Y-index) position). Similarly, equal or uneven arrangements may be applied to rows of the matrix corresponding to light with which the tissue is illuminated.

In some embodiments, the number of columns may be substantially larger than the number of rows, like more than 10 times, 100 times, or a 1000 times greater. In some embodiments, the number of rows may be, for example 3, like in some of the examples above with three different light sources that illuminate at three different wavelengths, two, one, or four or more, five or more, or 10 or more wavelengths. In some embodiments, the roles of rows and columns may be reversed, with row positions encoding emission wavelengths and column positions encoding illumination wavelengths.

In some embodiments, each sample in the training set may include multiple excitation-emission matrices, each corresponding to the same patient, and with one subset of the matrices of the sample corresponding to a body of tissue determined to be normal and another subset of the matrices corresponding to a body of tissue of the same patient being measured, like a suspicious mole or cancer. In some embodiments, only a one of these subsets of excitation-emission matrices is included, like the latter subset, and in some cases, that excitation-emission matrix is based upon both subsets, for instance, an average of one subtracted, in a matrix-position-by-matrix-position manner, from the other, thereby indicating a delta in the emission intensity for each excitation and emission wavelength between the baseline, normal, region and the suspicious region being measured. In some embodiments, each position in the excitation-emission matrix may include population statistics for a corresponding subset of other excitation-emission matrices upon which it is based, for instance indicating a measure of central tendency, like mean, median, or mode, and a measure of variation, like standard deviation, range, max and min, or variance.

Program code need not label data structures as "matrices" for a body of code to implement and excitation-emission matrix, provided that the relevant portions of the described information is present. For example, such matrices may be encoded as objects in an object-oriented programming language, key-value pairs, serialized hierarchical data structures, entries in relational databases, and the like, without the excitation-emission matrix being explicitly labeled as such in program code. Values in each position of the matrices may be encoded as light intensity, energy, bins in a histogram, nominal values in a classification, ordinal or cardinal values, or various other encodings that indicate light intensity in a range of wavelengths or specific wavelength.

In some embodiments, each sample in the training set includes one or more labels characterizing the measured tissue. Examples include nominal values, like types of diagnoses, such as text indicating that the measured tissue was determined to be a mole, normal tissue, or cancerous, for instance by a doctor, manually, or upon further observation over more than a week, month, or year. Examples include ordinal values, like rankings of a severity or development stage of cancer or other pathologies. Examples further include cardinal values, like measured concentrations of various materials determined to be present in the tissue. In some embodiments, labels may be indexed to a depth within the tissue from the surface of the tissue, in some cases with different labels corresponding to different depths. In some embodiments, labels may be handcrafted based upon analysis by trained medical professionals and lab results, for instance, from biopsies of tissues. In some cases, the labels may include population statistics, like those described above, corresponding to the different characterizations of the tissue, where multiple characterizations are made, like multiple lab tests, or multiple assessments by a panel of physicians.

In some embodiments, each sample in the training set includes other channels of information about the tissue. Examples include other types of optical measurements of the tissue, like photographic images of the tissue captured with a camera. Some embodiments, for instance, include a picture of a mole or potentially cancerous region that is associated with the excitation-emission matrix in the sample. Some embodiments may include such images at different ranges of wavelength, for instance one image in the visible spectrum and another in the infrared to reflect variation in body temperature. Some embodiments may include similar measurements of light transmitted through the tissue. Other examples include other types of measurements, like output of temperature probe, output of a miniaturized mass spectrometer sampling adjacent the tissue, measurements of the surface roughness of the tissue, and the like. In some cases, some or all of the measurements avoid removing or otherwise damaging any of the tissue being sampled, or some embodiments may extract a small portion of sample for processing, like in a microfluidic assay. In some cases, the machine learning model may be trained on these other channels as well, or a set of sub-models may be trained on different channels and merged together in an ensemble model that produces and aggregate classification or quantification based upon outputs of each of the sub-models, as described below.

Some embodiments may proceed to train a machine-learning model with the training set, as indicated by block 504. As mentioned, various types of machine learning models may be applied, and in some cases sub-models, like upstream models in a pipeline of models, may be trained before training downstream models based on their outputs. Some embodiments may implement transfer learning in which a pre-existing trained model or sub-model is obtained and parameter values thereof are adjusted (or parameters of a downstream model are adjusted) based on the training set, for instance, to reduce and aggregate amount of mis-classification while accommodating relatively sparse training sets. In some embodiments, the model is a supervised learning machine learning model, or some embodiments may implement unsupervised learning techniques, particularly those with access to relatively large training sets.

In some embodiments, the model is trained upon the raw or upon the normalized version of the obtained excitation-emission matrices and corresponding labels described above, for instance, including all of the values in the matrix. Or some embodiments may be trained upon hand-engineered features thereof, like particular bands of wavelengths and corresponding weights applied thereto or relationships there-between. Avoiding or reducing the amount of manually engineered features, however, is expected to produce more robust results, as there are often relatively subtle and complex relationships between the appropriate quantification or classification of a tissue and the types of measurements described herein.

As mentioned above, in some embodiments, the machine learning model is a multi-level neural network, for instance one trained with deep learning. Specific examples are illustrated in the figures of this application, and examples may include a plurality of perceptrons with various types of activation functions and parameters thereof that are adjusted during training. In some embodiments, the neural network is a member of a pipeline of machine learning models that are heterogeneous, for instance, with a non-convolutional multilevel neural network classifying or quantifying based upon excitation-emission matrices being paired with a convolutional neural network characterizing camera images, and both models feeding into a decision tree, like a classification tree trained with CART (classification and regression training), in some cases with the multilevel neural network and the convolutional neural network being separately trained, and then the decision tree being trained on the output of both with the same training set data or different subset thereof.

In some embodiments, the excitation-emission matrices may be used to train various types of models to produce outputs like the labels in the training set on novel (i.e., outside of the training set, or out of sample) excitation-emission matrices. In addition to multilevel neural networks, for instance with or without cycles in connections between neurons and with or without convolutional layers), embodiments may train and autoencoder machine learning model that maps the higher-dimensional excitation admission matrix into a lower-dimensional continuous vector space representation in which location in the vector space is indicative of classification or quantification like those in the labels. Some embodiments may train a triplet network or Siamese network. Such models may be particularly suitable where training sets are particularly sparse. For example, some embodiments may represent each excitation-emission matrix in the training set as a lower-dimensional vector (e.g., reducing from more than 100,000 dimensions of input variables of the input to between 10 and 1000 dimensions in a continuous vector space representation) in this vector space, and some embodiments may then, at inference time, determine which of these vectors is closest (in the vector space, for instance, by Euclidean distance, cosine angle, Minkowski distance, Manhattan distance, or various other measures) to a similarly constructed vector from a novel excitation-emission matrix to infer that similar labels should be applied to the out-of-sample excitation-emission matrix. Or some embodiments may cluster the excitation-emission matrix vectors from the training set during training, for instance with a clustering algorithm, like DB-SCAN, K-means, or various other clustering algorithms, and designate a convex hull of the clusters as being a region in the space corresponding to dominant (e.g., most common) labels within the cluster. At inference time, embodiments may then determine which of these regions include a vector output by the audio encoder responsive to a novel excitation-emission matrix to classify or quantify the corresponding body of tissue as having those dominant labels.

In another example, the excitation emission matrices in the training set may be used to train a decision tree (or classification tree, or regression tree for continuous variables, like quantities) or collection thereof like a random forest of decision trees. For example, parameters of such decision trees, like sequences of dimensions of the training samples and splits in those dimensions of the training samples may be determined with techniques like classification and regression tree (CART). Some embodiments may iteratively, with a greedy optimization, choose dimensions and splits thereof that tend to reduce an amount of impurity on either side of the split for the training set (or subset thereof), for instance, based upon Gini impurity or entropy computations of samples on each side of the candidate splits. (And these and various other loss functions may serve as the objective function for these or the other models described herein, e.g., some embodiments may apply categorical cross entropy as the loss function for spectra and focal loss for images). Each resulting region of the feature space that is segmented by this routine may be designated as corresponding to the dominant label values of the samples therein, for instance, with various regions being dominated by samples with cancer and other regions being dominated by samples with moles. Embodiments may then at inference time iterate through these dimensions and splits with a novel excitation-emission matrix and classify or quantify that matrix with the dominant label values in the region reached by applying these splits in the sequence of dimensions produced by training. Some embodiments may prune the decision trees by a threshold number of iterations after reaching a stopping condition to reduce the risk of overfitting the training data.

In another example, the excitation-emission matrices may be used to determine coefficients of a linear regression, for instance, with hand-engineered features. Some embodiments may determine coefficients that tend to reduce an amount of mischaracterization by the linear regression, for instance, with various optimization algorithms.

Some embodiments may implement training with a heterogeneous compute architecture, for instance, with a central processing unit paired with a separate (e.g., discrete or integrated) machine learning hardware accelerator. Examples include more general-purpose chips like graphics processing units, or those optimized for machine learning use cases, like tensor processing units, and the like. In some embodiments, the hardware accelerator has 8 or more cores, 16 bit or less (lower precision) floating point operations, represents model parameters during training in a floating radix point format (e.g., bfloat16), and implements an in-memory computing or dataflow architecture.

In the course of training, some embodiments may adjust parameters of the model being trained to optimize performance, as characterized by an objective function, on some or all of the training set. Examples include adjusting weights and biases of perceptrons in neural nets, selecting splits and dimensions to split in a decision tree, and the like. In some embodiments, the objective function is a loss or error function that indicates an aggregate amount of misclassification of the model in its current state of training relative to some or all of the training set. In another example, the objective functions of fitness function that indicates an aggregate amount of correct classification by the model in its current state of training relative to some or all of the training set. For example, some embodiments may compute a root mean square error relative to the training set, a rate of mis-classification, or a rate of correct classification.

Which model parameters are adjusted and the direction in which there are adjusted may be determined with a variety of techniques, examples including gradient descent, simulated annealing, and brute force optimization. Some embodiments may implement a greedy optimization that seeks to optimize performance relative to the objective function in a given iteration of training, and some embodiments may implement a global optimization the spans iterations. In some embodiments, the parameters may be initialized with a pseudorandom or random function before training, and training may be repeated over multiple iterations of training starting with different initialized parameters to guard against the risk of initial conditions resulting in optimization to a local maximum or minimum. Some embodiments may select a resulting instance of training that produces the best performance with respect to the objective function on some or all of the training data and use the trained parameters from that instance, discarding the others.

For example, some embodiments may apply a form of gradient descent, like stochastic gradient descent, for instance, with momentum to determine model parameters during training or with mini-batch gradient descent. Some embodiments may iteratively adjust model parameters by a designated amount, set as a hyper parameter (or model parameter that is not varied during an instance of training as a result of the training set, but which may be changed between training instances as needed), during each iteration of a given training instance. In some embodiments, the direction of adjustment may be computed by determining a partial derivative of the respective parameter with respect to the objective function, thereby indicating a slope in a higher dimensional space (e.g., with as many dimensions as there are model parameters) that can indicate a direction in which local changes will tend to optimize the models performance with respect to the objective function. Some embodiments may repeatedly make such adjustments through a plurality of iterations in a given instance of training until a stopping condition is detected. Examples of stopping conditions include determining that more than a threshold number of iterations have been performed or that the aggregate measure of performance of the model, for instance, as characterized by the objective function has changed by less than a threshold amount between iterations, thereby potentially indicating the local maximum or minimum, depending upon whether a loss or a fitness function serves as the objective function.

A variety of techniques can be used to enhance the performance of the model for a given sized training set. Some embodiments may implement techniques like bootstrap aggregation, boosting, cross validation, and the like. Some embodiments may, for example, repeatedly train the model on different subsets of the training set, for instance, forming the subsets by sampling with or without replacement from the training set randomly to form the subsets, and then training on the results. Some embodiments may then form an ensemble model that aggregates the result of the various training instances, or some embodiments may compute a measure of central tendency for model parameters among the various instances of training. Some embodiments may hold in reserve a subset of the training set for cross validation, and not use the subset held in reserve during training, until validating the model after training to gauge whether the model generalizes out of sample. Some embodiments may determine whether the model achieves greater than a threshold level of performance on the portion of training data held in reserve, for instance with respect to type I errors, type II errors, F1 scores, or other measures of performance.

Some embodiments may then load the trained model to a run-time environment, as indicated by block 506. In some cases, training may occur on a substantially more performant system than that used for inference at runtime, when making inferences based on out-of-sample, or novel, data from new patients. For example, training may occur on relatively powerful servers in a data center while inference may be performed on resource constrained hand-held computing devices in the field. Or, as discussed below, in some cases inference may be performed remote from where measurements are taken on more powerful computing hardware. In some cases, the model parameters, like weights and biases of perceptrons, may be stored in memory of the computing systems that well make inferences on novel measurements from out of sample tissues, like those that were not present in the training set, for instance after the system is deployed to doctors' offices.

Some embodiments may then obtain an excitation-commission matrix of a new measurement of a tissue, as indicated by block 508. In some embodiments, the new measurement is produced by a device like those described above upon a patient presenting in a doctor's office and undergoing the measurement. In some cases, this may happen days or weeks or longer after the previous step, which is not to suggest that time limits between the other steps apply. In some embodiments, the excitation-emission matrix is received with additional channels of information like those described above with respect to the training sets from a device having various types of sensors (cameras, temperature probes, miniaturized mass spectrometers, and the like).

In some embodiments, steps 508 through 514 are executed on a processor on a hand-held or desk-top computing device in a physician's office. In some embodiments, a hand-held device (like device 100) makes the measurements described, and a local computing device in the doctor's office wireless area network or local area network executes these operations. Or in some cases, such devices may send to the measurement data to a remote server system that executes steps 508-512 and causes step 514 upon receiving the matrix via a network, such as over the Internet. In some embodiments, the matrix is obtained in real-time, for instance within 10 minutes, like two minutes, or within two seconds or 500 ms of when the measurement is taken.

In some cases, the obtained matrix is a set of matrices like those described above, such as a reference baseline measurement of a normal region of the patient and a measurement of a region under test, such as a concerning mark on the patient's body, or some embodiments may receive a single matrix corresponding to the latter. In some embodiments, the obtained matrix is the result of a transformation based on one or more these matrices, like a delta therebetween indicating differences in emission spectra between the baseline region and the tested region and various population statistics like those described above. In some embodiments, the obtained matrix is part of a scan in which each matrix is associated with an indication of location on the patient's body, like a polar coordinate for a radial scan or Cartesian coordinate paired with a height along the patient, in some cases with additional dimensions indicating additional information about light-based sensor pose relative to the patient. In some embodiments, the results may be indexed to position on the patient's body to form a map display, like a heat map indicating variations in output over the patient's body.

Some embodiments may then infer a classification or quantification of the tissue with the trained model, as indicated by block 510. In some embodiments, the obtained data may undergo various transformations before being input into the model, such as calculating various engineered features, normalizing input features to fall within a range of values, excluding outliers, and the like. Some input features, both during training and during inference, may include other attributes of the patient supplied by the physician, like demographic attributes, age, skin tone, region of the body being scanned, and the like. In some cases, inputs may further include calibration data in memory for the specific spectrograph, like measurements against a sample with known properties that can be used to measure drift in the sensor.

In some embodiments, the input features may cause a cascade of outputs through the model that produces output values indicative of a classification or quantification, like the various types of outputs described above with reference to training. In some embodiments, inference may be performed on a machine learning hardware inference accelerator, like an edge tensor processing unit, a graphics processing unit, a bionic neural engine chip from Apple Inc., or other computing device paired with a central processing unit to expedite the execution of the model. In some cases, the resulting inference is obtained in real-time, for instance within less than 30 seconds, like within less than two seconds, and in some cases, within less than 50 ms of receiving the inputs to the model.

As indicated above, some embodiments may include providing different subsets of the inputs to different trained sub-models, the outputs of which may be propagated through pipeline of models to a downstream sub-model that aggregates their outputs and produces an aggregate output in an ensemble model. As mentioned, in some cases inference is executed locally, on a processor of the device taking the measurement, or remotely upon the measured data being sent to a different, possibly higher performance computing device over a network. And as mentioned, in some cases the inferences executed in real-time, or after some delay, for instance as part of a batch process. In some cases, the obtained inputs may be obtained without a label like those described above as having been associated with the training set, and some embodiments may output labels like those described above in association with the training sets.

Some embodiments may then store the result in memory of the computing device making the inference, as indicated by block 512, and some embodiments may cause results to be displayed, as indicated by block 514. For example, some embodiments may cause results to be displayed on a display of a hand-held measurement device like those described above, either via local operation of an onboard processor or by sending instructions over a network from a remote server to the handheld device to cause a display to be presented. In some cases, the display may indicate values like the above-described labels, in some cases with confidence values indicating a reliability of the output inferred by the model. Some embodiments may cause the inputs and/or the outputs to be written to an electronic medical record system, for instance, via the FHIR API and associated with a patient identifier, for instance, supplied via an interface of the measurement device. Some embodiments may further cause a patient or an insurance company or both to be invoiced for the measurement routine, and some embodiments may later query the electronic medical record system to obtain information about later developments for the patient to detect mis-classifications and augment the training set.

FIG. 9 is a diagram that illustrates an exemplary computing system 1000 in accordance with embodiments of the present technique. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010*a*-1010*n*) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010*a*), or a multi-processor system including any number of suitable processors (e.g., 1010*a*-1010*n*). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computer system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computer system 1000 through a wired or wireless connection. I/O devices 1060 may be connected to computer system 1000 from a remote location. I/O devices 1060 located on remote computer system, for example, may be connected to computer system 1000 via a network and network interface 1040.

Network interface 1040 may include a network adapter that provides for connection of computer system 1000 to a network. Network interface may 1040 may facilitate data exchange between computer system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors $1010a$-$1010n$) to implement one or more embodiments of the present techniques. Instructions 1100 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors $101a$-$1010n$) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1050 may be configured to coordinate I/O traffic between processors $1010a$-$1010n$, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors $101a$-$1010n$). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 1000 or multiple computer systems 1000 configured to host different portions or instances of embodiments. Multiple computer systems 1000 may provide for parallel or sequential processing/execution of one or more portions of the techniques described herein.

Those skilled in the art will appreciate that computer system 1000 is merely illustrative and is not intended to limit the scope of the techniques described herein. Computer system 1000 may include any combination of devices or software that may perform or otherwise provide for the performance of the techniques described herein. For example, computer system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 1000 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A system, comprising: one or more processors; and memory storing instructions that, when executed by at least some of the processors, effectuate operations comprising: obtaining an excitation-emission matrix, wherein the excitation-emission matrix is measured with a spectrometer by: illuminating a biological tissue with stimulant light at a first wavelength to cause a first fluorescent emission of light by the biological tissue, measuring a first set of intensities of the first fluorescent emission of light at a plurality of different respective emission wavelengths, illuminating the biological tissue with stimulant light at a second wavelength to cause a second fluorescent emission of light by the biological tissue, and measuring a second set of intensities of the second fluorescent emission of light at a plurality of different respective emission wavelengths; inferring a classification of the biological tissue or a concentration of a substance in the biological tissue with a machine learning model trained on excitation-emission matrices in a labeled training set with supervised learning; and storing the classification of the biological tissue or the concentration of the substance in memory.

2. The system of embodiment 1, comprising: the spectrometer, wherein the spectrometer comprises a processor and memory storing instructions that, when executed by the processor of the spectrometer, effectuate the measurement of the excitation-emission matrix, wherein: the excitation-emission matrix is measured by the spectrometer by: illuminating the biological tissue with stimulant light at a third wavelength to cause a third fluorescent emission of light by the biological tissue, and measuring a third set of intensities of the third fluorescent emission of light at a plurality of different respective emission wavelengths; the first set of intensities are measured, at least in part, before illuminating the biological tissue with stimulant light at the second wavelength; the second set of intensities are measured, at least in part, before illuminating the biological tissue with stimulant light at the third wavelength; and a first portion of the biological tissue measured with stimulant light at the first wavelength at least partially overlap a second portion of the biological tissue measured with stimulant light at the second wavelength.

3. The system of embodiment 2, wherein: memory of the spectrometer comprises the machine learning model; and the one or more processors are the processor of the spectrometer.

4. The system of embodiment 2, wherein the spectrometer comprises: three lasers/laser diodes configured to output, responsive to control signals from the processor of the spectrometer, three different wavelengths of stimulant light, the three different wavelengths comprising: stimulant light at the first wavelength, stimulant light at the second wavelength, and stimulant light at the third wavelength; a waveguide configured to be placed adjacent the biological tissue and conduct light from the first fluorescent emission, the second fluorescent emission, and the third fluorescent emission to a diffraction grating of the spectrometer; and a set of light sensors communicatively coupled to the processor of the spectrometer and positioned to be illumined by an output of the diffraction grating and measure the first set of intensities, the second set of intensities, and the third set of intensities.

5. The system of any one of embodiments 1-5, wherein: the spectrometer is a hand-held spectrometer having an on-board power supply and a display configured to display an indication of the classification of the biological tissue or the concentration of the substance.

6. The system of any one of embodiments 1-5, wherein: the first wavelength is within a range of 300-400 nanometers (nm); the second wavelength is within a range of 500-600 nm; and the third wavelength is within a range of 650-850 nm.

7. The system of any one of embodiments 1-6, wherein the machine/deep learning model comprises a multi-layer neural network that comprises: an input layer; a first hidden layer coupled to an output of the input layer; a second hidden layer coupled to an output of the first hidden layer; and an output layer implementing a SoftMax function.

8. The system of embodiment 7, wherein different activation functions are used in different layers of the multi-layer neural network.

9. The system of embodiment 8, wherein the different activation functions comprise: a rectified linear unit activation function; a sigmoid activation function; and a hyperbolic tangent activation function.

10. The system of embodiment 7, wherein: the first set of intensities, the second set of intensities, and the third set of intensities each comprise more than 500 different intensity measurements at different wavelengths; the multi-layer neural network comprises more than 50,000 weights and biases; and the second hidden layer is larger than the first hidden layer.

11. The system of any one of embodiments 1-19, wherein: obtaining the excitation-emission matrix comprises receiving the excitation-emission matrix from the spectrometer over a network; and the one or more processors are part of a server system that is remote from the spectrometer and is configured to process excitation-emission matrices from a plurality of different spectrometers operated by different medical professionals in different geographic locations.

12. The system of any one of embodiments 1-11, wherein the machine learning model comprises a multi-layer neural network that is trained with operation comprising: obtaining the training set comprising excitation-emission matrices labeled with values indicating whether the excitation-emission matrices characterize emissions from a cancerous or non-cancerous tissue; assigning initial values to parameters of the multi-layer neural network; iteratively, until a stopping condition is detected, performing operations comprising: for each of at least some parameters the multi-layer neural network, determining a partial derivative of an objective function with respect to the respective parameter, the objective function indicating an aggregate amount of misprediction of the multi-layer neural network in a current state relative to labels of at least part of the training set; and for each of at least some parameters of the multi-layer neural network, adjusting respective parameters in a respective direction that a corresponding partial derivative indicates tends to locally optimize the multi-layer neural network with respect to the objective function.

13. The system of embodiment 12, the operations comprising: performing the training a first time with a first subset of the training set; performing the training a second time with a second subset of the training set; and selecting values for parameters of the multi-layer neural network based on whether training the multi-layer neural network the first time or the second time produces more accurate performance when measured against a third subset of the training set.

14. The system of any one of embodiments 1-13, wherein: the biological tissue is human skin; and inferring the classification of the biological tissue or concentration of the substance in the biological tissue comprises classifying the biological tissue into one of a set of classes including: normal tissue, a mole, and cancer.

15. The system of any one of embodiments 1-14, wherein: the one or more processors comprise a machine-learning hardware accelerator having 16 bits or less precision of floating point operations on data in a floating radix point format in 8 or more cores; and at least part of the machine learning model is executed by the machine-learning hardware accelerator.

16. The system of any one of embodiments 1-15, wherein: a plurality of excitation-emission matrices are obtained, each corresponding to a different location on a human body in a scanned region; and inferring the classification of the biological tissue or concentration of the substance in the biological tissue comprises forming a map of classification probability or concentration of the substance in the scanned region and causing the map to be displayed.

17. The system of any one of embodiments 1-16, wherein: excitation-emission matrix is formed by comparing excitation-emission matrices from control and tested regions of the tissue.

18. The system of any one of embodiments 1-17, wherein: the excitation-emission matrix is obtained with a corresponding image of the biological tissue; and the machine learning model comprises a multi-layer dense neural network configured to classify the image and output a feature to an ensemble model that combines classifications based on the image and the excitation-emission matrix in an aggregate output classification of the biological tissue.

19. The system of any one of embodiments 1-19, comprising: means for fluorescence spectroscopy.

20. A method of classifying a tissue, the method comprising: sequentially illuminating a tissue with a plurality of light sources; detecting, with a spectrometer waveguide, emitted light from the tissue as a result of illumination with the plurality of light sources; obtaining, with a data processor, a set of fluorescence spectra from the emitted light; classifying the tissue into a specific tissue type, by using a machine learning model, into a plurality of tissue types based on intensity of the set of fluorescence spectra; and displaying the tissue type in a user interface.

21. The method of embodiment 20, wherein: the plurality of tissue types comprises normal tissue, cancerous tissue, and a mole; each light source of the plurality of light sources emits substantially monochromatic light or incoherent light filtered to a specific wavelength, the specific wavelength of each light source of the plurality of light sources is configured to be tunable; and intensity of each light source of the plurality of light sources is configured to be tunable.

22. The method of any one of embodiments 20-21, wherein the spectrometer comprises a polychromator integrated with a reflection grating and a complementary metal oxide semiconductor (CMOS) linear image sensor.

23. The method of any one of embodiments 20-23, wherein: the tissue is skin tissue; and a gel is applied on the skin tissue before illumination to provide a homogenous medium between the skin tissue and the plurality of light sources.

24. The method of any one of embodiments 20-23, wherein: illumination of each of the plurality of light sources is carried out for a threshold duration of time specified by user input; the plurality of light sources comprises 6 light sources; a first and a second light source among the 6 light sources have wavelengths within the range of 300-400 nm; a third and a fourth light source among the 6 light sources have wavelengths within the range of 500-600 nm; and a fifth and a sixth light source among the 6 light sources have wavelengths within the range of 650-850 nm.

25. The method of embodiment 24, wherein the plurality of light sources and the spectrometer waveguide are located in a single probe with the spectrometer waveguide in the middle and the plurality of light sources positioned circumferentially around the spectrometer waveguide with equal spacing.

26. The method of any one of embodiments 20-25, wherein the illuminating is performed in vivo.

27. The method of any one of embodiments 20-26, wherein the illuminating is performed in vitro.

28. The method of any one of embodiments 20-27, wherein classifying comprises pre-processing the set of fluorescence intensity spectra by: normalizing the set of fluorescence spectra to its respective maximum intensity; and separating the normalized set of fluorescence spectra into individual wavelengths.

29. The method of any one of embodiments 20-29, wherein classifying further comprises: determining the type of tissue by comparing the fluorescence spectra to fluorescence spectra of at least 100 normal tissue, 100 moles and birthmarks, and 100 cancerous tissue samples.

30. The method of any one of embodiments 20-29, wherein a plurality of fluorescence biochemical markers are used to increase the intensity of fluorescence emission.

31. The system of any one of embodiments 1-20, comprising: an endoscope through which information about the first fluorescent emission of light and the second fluorescent emission of light are communicated, wherein: inferring the classification of the biological tissue or concentration of the substance in the biological tissue comprises determining whether the biological tissue includes lung cancer, bladder cancer, oral cancer, or thyroid cancer.

What is claimed is:

1. A system, comprising:
a spectrometer;
one or more processors; and
memory storing instructions that, when executed by at least some of the processors, effectuate operations comprising:
obtaining an excitation-emission matrix, wherein the excitation-emission matrix is measured with the spectrometer by:
illuminating a biological tissue with stimulant light at a first wavelength to cause a first fluorescent emission of light by the biological tissue,
measuring a first set of intensities of the first fluorescent emission of light at a plurality of different respective emission wavelengths, wherein the first set of intensities comprises a first group of more than 500 different intensity measurements of different wavelengths;
illuminating the biological tissue with stimulant light at a second wavelength to cause a second fluorescent emission of light by the biological tissue, and
measuring a second set of intensities of the second fluorescent emission of light at a plurality of different respective emission wavelengths, wherein the second set of intensities comprises a second group of more than 500 different intensity measurements of different wavelengths;
illuminating the biological tissue with stimulant light at a third wavelength to cause a third fluorescent emission of light by the biological tissue, and
measuring a third set of intensities of the third fluorescent emission of light at a plurality of different respective emission wavelengths, wherein the third set of intensities comprises a third group of more than 500 different intensity measurements at different wavelengths;
inferring a classification of the biological tissue or a concentration of a substance in the biological tissue with a machine learning model trained with deep learning on excitation-emission matrices in a labeled training set with supervised learning, wherein the machine learning model comprises a multi-layer neural network that comprises:
more than 50,000 weights and biases;
an input layer;
a first hidden layer coupled to an output of the input layer;
a second hidden layer coupled to an output of the first hidden layer, wherein the second hidden layer is larger than the first hidden layer; and
an output layer implementing a SoftMax function;
storing the classification of the biological tissue or the concentration of the substance in memory.

2. The system of claim 1,
wherein the spectrometer comprises a processor and memory storing instructions that, when executed by the processor of the spectrometer, effectuate the measurement of the excitation-emission matrix, wherein:
the excitation-emission matrix is measured by the spectrometer by:
illuminating the biological tissue with stimulant light at a third wavelength to cause a third fluorescent emission of light by the biological tissue, and
measuring a third set of intensities of the third fluorescent emission of light at a plurality of different respective emission wavelengths;
the first set of intensities are measured, at least in part, before illuminating the biological tissue with stimulant light at the second wavelength;
the second set of intensities are measured, at least in part, before illuminating the biological tissue with stimulant light at the third wavelength; and
a first portion of the biological tissue measured with stimulant light at the first wavelength at least partially overlap a second portion of the biological tissue measured with stimulant light at the second wavelength.

3. The system of claim 2, wherein:
memory of the spectrometer comprises the machine learning model; and
the one or more processors are the processor of the spectrometer.

4. The system of claim 2, wherein the spectrometer comprises:
three lasers including laser diodes and configured to output, responsive to control signals from the processor of the spectrometer, three different wavelengths of stimulant light, the three different wavelengths comprising: stimulant light at the first wavelength, stimulant light at the second wavelength, and stimulant light at the third wavelength;
a waveguide configured to be placed adjacent the biological tissue and conduct light from the first fluorescent emission, the second fluorescent emission, and the third fluorescent emission to a diffraction grating of the spectrometer; and
a set of light sensors communicatively coupled to the processor of the spectrometer and positioned to be illumined by an output of the diffraction grating and measure the first set of intensities, the second set of intensities, and the third set of intensities.

5. The system of claim 1, wherein:
the spectrometer is a hand-held spectrometer having an on-board power supply and a display configured to display an indication of the classification of the biological tissue or the concentration of the substance.

6. The system of claim 1, wherein:
the first wavelength is within a range of 300-400 nanometers (nm);
the second wavelength is within a range of 500-600 nm; and
the third wavelength is within a range of 650-850 nm.

7. The system of claim 1, wherein different activation functions are used in different layers of the multi-layer neural network.

8. The system of claim 7, wherein the different activation functions comprise:
a rectified linear unit activation function;
a sigmoid activation function; and
a hyperbolic tangent activation function.

9. The system of claim 1, wherein:
obtaining the excitation-emission matrix comprises receiving the excitation-emission matrix from the spectrometer over a network; and
the one or more processors are part of a server system that is remote from the spectrometer and is configured to process excitation-emission matrices from a plurality of different spectrometers operated by different medical professionals in different geographic locations.

10. The system of claim 1, wherein the machine learning model comprises a multi-layer neural network that is trained with operation comprising:
obtaining the training set comprising excitation-emission matrices labeled with values indicating whether the excitation-emission matrices characterize emissions from a cancerous or non-cancerous tissue;
assigning initial values to parameters of the multi-layer neural network;
iteratively, until a stopping condition is detected, performing operations comprising:
for each of at least some parameters the multi-layer neural network, determining a partial derivative of an objective function with respect to the respective parameter, the objective function indicating an aggregate amount of mis-prediction of the multi-layer neural network in a current state relative to labels of at least part of the training set; and
for each of at least some parameters of the multi-layer neural network, adjusting respective parameters in a respective direction that a corresponding partial derivative indicates tends to locally optimize the multi-layer neural network with respect to the objective function.

11. The system of claim 10, the operations comprising:
performing the training a first time with a first subset of the training set;
performing the training a second time with a second subset of the training set; and
selecting values for parameters of the multi-layer neural network based on whether training the multi-layer neural network the first time or the second time produces more accurate performance when measured against a third subset of the training set.

12. The system of claim 1, wherein:
the biological tissue is human skin; and
inferring the classification of the biological tissue or concentration of the substance in the biological tissue comprises classifying the biological tissue into one of a set of classes including: normal tissue, a mole, and cancer.

13. The system of claim 1, wherein:
the one or more processors comprise a machine-learning hardware accelerator having 16 bits or less precision of floating point operations on data in a floating radix point format in 8 or more cores; and
at least part of the machine learning model is executed by the machine-learning hardware accelerator.

14. The system of claim 1, wherein:
a plurality of excitation-emission matrices are obtained, each corresponding to a different location on a human body in a scanned region; and
inferring the classification of the biological tissue or concentration of the substance in the biological tissue comprises forming a map of classification probability or concentration of the substance in the scanned region and causing the map to be displayed.

15. The system of claim 1, wherein:
the excitation-emission matrix is formed by comparing the intensity measurements from control and tested regions of the tissue.

16. The system of claim 1, wherein:
the excitation-emission matrix is obtained with a corresponding image of the biological tissue; and
the machine learning model comprises a multi-layer dense neural network configured to classify the image and output a feature to an ensemble model that combines classifications based on the image and the excitation-emission matrix in an aggregate output classification of the biological tissue.

17. The system of claim 1, comprising:
means for fluorescence spectroscopy.

18. The system of claim 1, comprising:
an endoscope through which information about the first fluorescent emission of light and the second fluorescent emission of light are communicated, wherein:
inferring the classification of the biological tissue or concentration of the substance in the biological tissue comprises determining whether the biological tissue includes lung cancer, bladder cancer, oral cancer, or thyroid cancer.

19. A method of classifying a tissue, the method comprising:
sequentially illuminating a tissue with a plurality of light sources of a spectrometer;
detecting, with a spectrometer waveguide, emitted light from the tissue as a result of illumination with the plurality of light sources;
obtaining, with a data processor, a set of fluorescence spectra from the emitted light, the set of fluorescence spectra including a first set of intensities produced by stimulant light among the plurality of light sources at a first wavelength, a second set of intensities produced by stimulant light among the plurality of light sources at a second wavelength, and a third set of intensities produced by stimulant light among the plurality of light sources at a third wavelength, wherein the first set of intensities, the second set of intensities, and the third set of intensities each comprise more than 500 different intensity measurements at different wavelengths;
classifying the tissue into a specific tissue type, by using a machine learning model, into a plurality of tissue types based on intensity of the set of fluorescence spectra, wherein the machine learning model is trained with deep learning on excitation-emission matrices in a labeled training set with supervised learning and, wherein:
the machine learning model comprises a multi-layer neural network that comprises: an input layer, a first hidden layer coupled to an output of the input layer, a second hidden layer coupled to an output of the first hidden layer, and an output layer implementing a SoftMax function;
the multi-layer neural network comprises more than 50,000 weights and biases; and
the second hidden layer is larger than the first hidden layer; and
displaying the tissue type in a user interface.

20. The method of claim 19, wherein:
the plurality of tissue types comprises normal tissue, cancerous tissue, and a mole;
each light source of the plurality of light sources emits substantially monochromatic light or incoherent light filtered to a specific wavelength;
the specific wavelength of each light source of the plurality of light sources is configured to be tunable; and
intensity of each light source of the plurality of light sources is configured to be tunable.

21. The method of claim 19, wherein the spectrometer comprises a polychromator integrated with a reflection grating and a complementary metal oxide semiconductor (CMOS) linear image sensor.

22. The method of claim 19, wherein:
the tissue is skin tissue; and
a gel is applied on the skin tissue before illumination to provide a homogenous medium between the skin tissue and the plurality of light sources.

23. The method of claim 19, wherein:
illumination of each of the plurality of light sources is carried out for a threshold duration of time specified by user input;
the plurality of light sources comprises 6 light sources;
a first and a second light source among the 6 light sources have wavelengths within a first range of 300-400 nm;
a third and a fourth light source among the 6 light sources have wavelengths within a second range of 500-600 nm; and
a fifth and a sixth light source among the 6 light sources have wavelengths within a third range of 650-850 nm.

24. The method of claim 23, wherein the plurality of light sources and the spectrometer waveguide are located in a single probe with the spectrometer waveguide at a middle location on the single probe and the plurality of light sources positioned circumferentially around the spectrometer waveguide with equal spacing.

25. The method of claim 19, wherein the illuminating is performed in vivo.

26. The method of claim 19, wherein the illuminating is performed in vitro.

27. The method of claim 19, wherein classifying comprises pre-processing the set of fluorescence intensity spectra by:
normalizing the set of fluorescence spectra to its respective maximum intensity; and
binning the normalized set of fluorescence spectra into individual wavelengths.

28. The method of claim 19, wherein classifying further comprises:
determining the type of tissue by comparing the fluorescence spectra to fluorescence spectra of at least 100 normal tissue, 100 moles or birthmarks, and 100 cancerous tissue samples.

29. The method of claim 19, wherein a plurality of fluorescence biochemical markers are used to increase the intensity of fluorescence emission.

* * * * *